(12) United States Patent
Barrelli et al.

(10) Patent No.: US 8,715,236 B2
(45) Date of Patent: May 6, 2014

(54) MOBILE INFUSION DEVICE

(71) Applicants: Aharon Ronny Barrelli, Thornhill, CA (US); Kevin Bailey, Ottawa (CA); Matthew Bailey, Ottawa (CA); Gautam Sayal, Ottawa (CA); Robert Dickie, King City (CA)

(72) Inventors: Aharon Ronny Barrelli, Thornhill, CA (US); Kevin Bailey, Ottawa (CA); Matthew Bailey, Ottawa (CA); Gautam Sayal, Ottawa (CA); Robert Dickie, King City (CA)

(73) Assignee: TrendyMED Inc., Thornhill (CA)

( * ) Notice: Subject to any disclaimer, the term of this patent is extended or adjusted under 35 U.S.C. 154(b) by 13 days.

(21) Appl. No.: 13/690,862

(22) Filed: Nov. 30, 2012

(65) Prior Publication Data
US 2013/0237915 A1  Sep. 12, 2013

Related U.S. Application Data

(60) Provisional application No. 61/566,397, filed on Dec. 2, 2011.

(51) Int. Cl.
*A61M 37/00* (2006.01)
*A61M 5/142* (2006.01)
*B65D 83/00* (2006.01)
*A61M 5/148* (2006.01)

(52) U.S. Cl.
CPC ....... *A61M 5/14232* (2013.01); *B65D 83/0061* (2013.01); *A61M 5/142* (2013.01); *A61M 5/148* (2013.01)
USPC ....................................... 604/131; 417/477.8

(58) Field of Classification Search
CPC . A61M 5/142; A61M 5/14232; A61M 5/148; A61J 1/10; B65D 83/0061
USPC ................................ 417/477.8; 604/131, 136
See application file for complete search history.

(56) References Cited

U.S. PATENT DOCUMENTS 3,151,616 A  10/1964 Selfon
3,647,117 A   3/1972 Hargest
(Continued)

FOREIGN PATENT DOCUMENTS

CA     2083555 A1    5/1994
JP    2001-170175 A  6/2001
(Continued)

OTHER PUBLICATIONS

International Search Report and Written Opinion for PCT/CA2012/001103 mailed Mar. 26, 2013.

*Primary Examiner* — Nicholas Lucches
*Assistant Examiner* — Gerald Landry, II
(74) *Attorney, Agent, or Firm* — Bereskin & Parr LLP/S.E.N.C.R.L., s.r.l.

(57) ABSTRACT

Various embodiments are described herein for a mobile infusion device that does not use gravity to expel fluid from a bag. The device has a housing with a central chamber connected with an opening to receive a portion of the bag during use. A rotation assembly is coupled to the housing and includes at least one roller located within the central chamber and a spring mechanism operatively coupled to the at least one roller to rotate it to move the bag and apply a force to a portion of the bag to expel fluid therefrom during use. A control mechanism is operatively coupled to the rotation assembly and has a control assembly to control rotation of the rotation assembly and a user interface coupled to the control assembly to allow a user to select a mode of operation for the device. The spring mechanism is recharged in standby mode. Various mechanisms can be used in various embodiments to improve functionality such as a gearing mechanism.

36 Claims, 20 Drawing Sheets

(56) References Cited

U.S. PATENT DOCUMENTS

| | | | |
|---|---|---|---|
| 4,044,764 A * | 8/1977 | Szabo et al. | 604/134 |
| 4,772,263 A | 9/1988 | Dorman et al. | |
| 4,850,971 A * | 7/1989 | Colvin | 604/134 |
| 4,968,301 A | 11/1990 | di Palma et al. | |
| 5,330,431 A * | 7/1994 | Herskowitz | 604/153 |
| 5,490,613 A | 2/1996 | Taylor et al. | |
| 5,560,518 A * | 10/1996 | Catterall et al. | 222/99 |
| 5,578,001 A | 11/1996 | Shah | |
| 5,728,077 A | 3/1998 | Williams et al. | |
| 5,776,105 A | 7/1998 | Corn | |
| 6,645,176 B1 | 11/2003 | Christenson et al. | |
| 6,669,668 B1 * | 12/2003 | Kleeman et al. | 604/131 |
| 7,789,853 B2 | 9/2010 | Kriesel | |
| 2001/0016710 A1 * | 8/2001 | Nason et al. | 604/153 |
| 2012/0022456 A1 * | 1/2012 | Salgia et al. | 604/181 |
| 2013/0160654 A1 * | 6/2013 | Agon | 99/295 |

FOREIGN PATENT DOCUMENTS

| | | |
|---|---|---|
| JP | 2001-259027 A | 9/2001 |
| WO | 2013/078545 A1 | 6/2013 |

\* cited by examiner

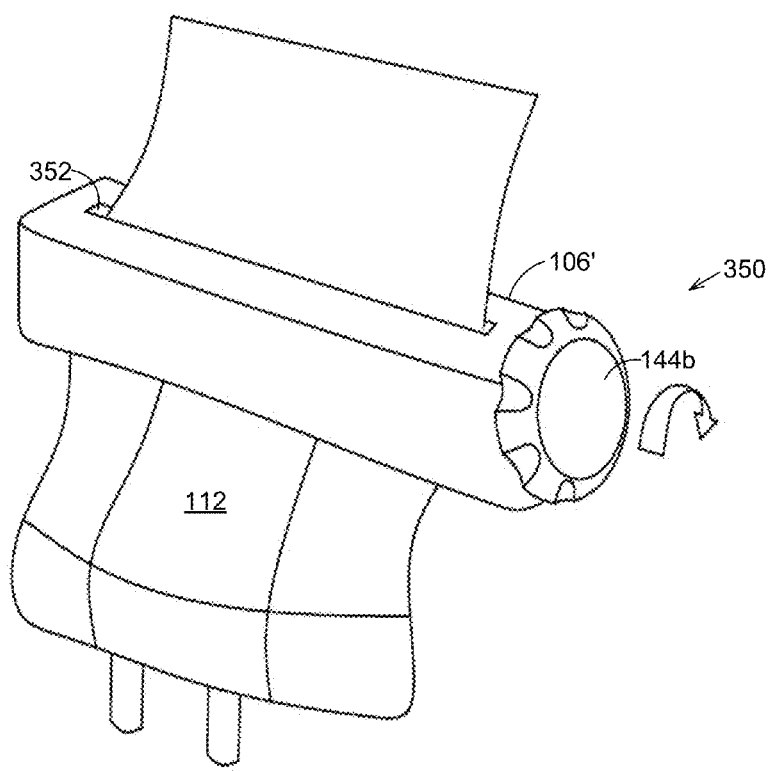
FIG. 5A
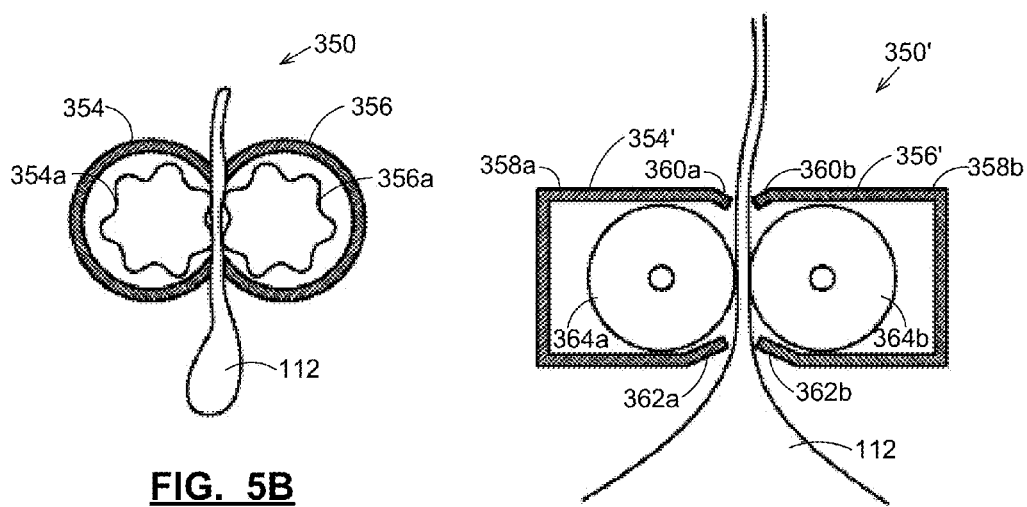
FIG. 5B
FIG. 5C

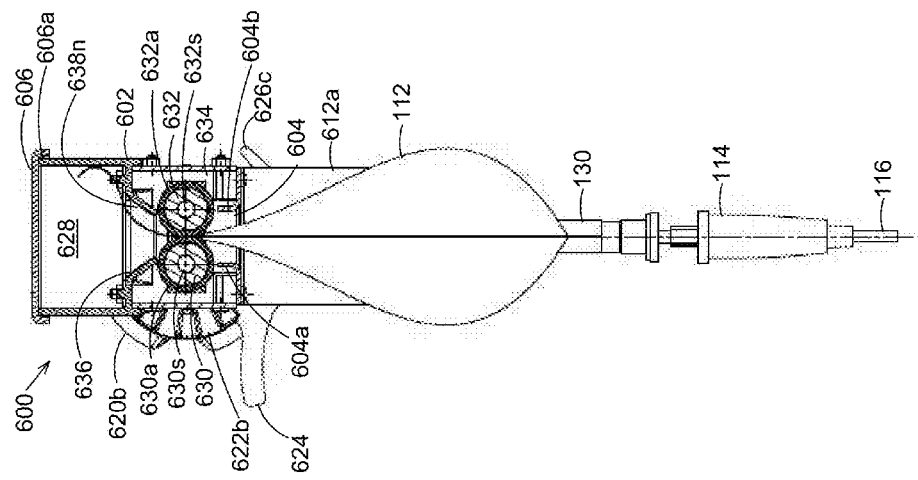
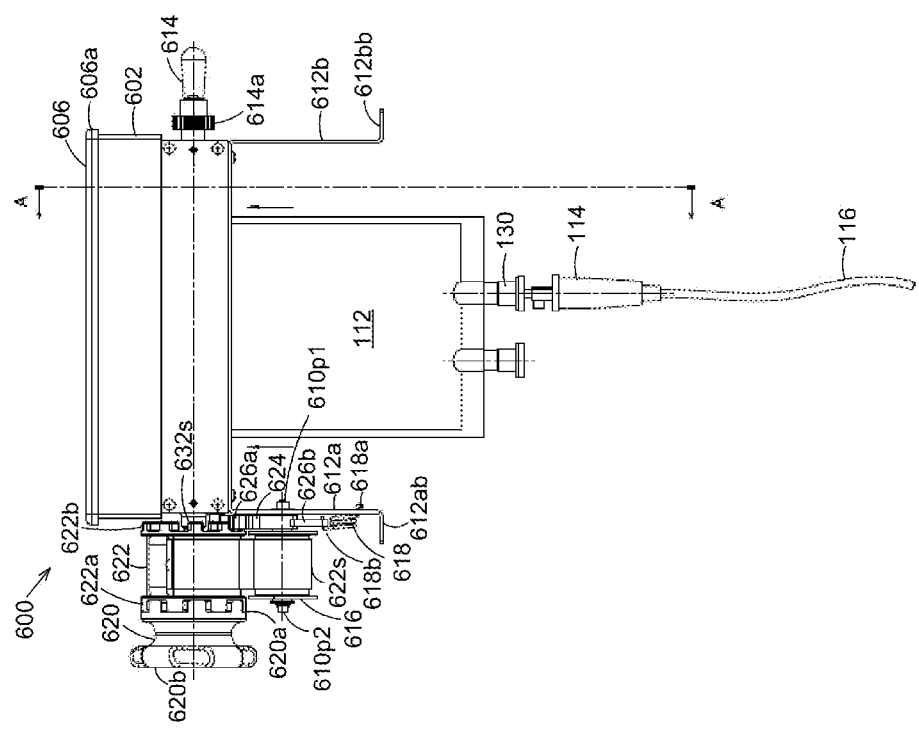

MOBILE INFUSION DEVICE

CROSS-REFERENCE TO RELATED APPLICATION

This application claims the benefit of U.S. Provisional Application No. 61/566,397, filed on Dec. 2, 2011, the contents of which are hereby incorporated by reference.

FIELD

Various embodiments are described herein relating to a mobile infusion device.

BACKGROUND

Intravenous (IV) infusion therapy is used to infuse fluids to a patient at an effectively constant rate over a specified interval of time. Accordingly, IV infusion therapy may be used for various purposes in a wide variety of situations. However, much of global IV infusion is still delivered through conventional IV poles using gravity. This is likely due to its simplicity and not because of its ease of use. Unfortunately, patients using IV poles are mostly confined to their bed because of the clumsiness and difficulty in mobilizing and navigating the IV pole.

There are various negative aspects of IV infusion therapy when conventional IV infusion devices are used. For example, although many IV patients are bedridden, it may not always be necessary for the patient to remain lying down during infusion therapy. Indeed, but for limitations imposed by the conventional infusion devices being used, there may be no need for the patient to remain non-ambulatory for the prolonged periods of time that may be necessary for IV therapy. However, if the patient were able to move around during IV therapy it may reduce the recovery time of the patient which will help reduce hospital bills and the burden on the healthcare system while increasing patient through-put.

SUMMARY

In one aspect, at least one embodiment described herein provides a mobile infusion device that does not use gravity to expel fluid from a bag, wherein the mobile infusion device comprises a housing including a first portion shaped to define a central chamber in the housing and a second portion shaped to define a first opening in the housing that is in communication with the central chamber and adapted to receive a portion of the bag during use; a rotation assembly coupled to the housing, the rotation assembly including at least one roller located within the central chamber and a spring mechanism operatively coupled to the at least one roller to rotate the at least one roller in order to move the bag and apply a force to a portion of the bag to expel fluid from the bag during use; and a control mechanism operatively coupled to the rotation assembly, the control mechanism having a control assembly to control rotation of the rotation assembly and a user interface coupled to the control assembly to allow a user to select one of a start mode, a stop mode and a standby mode for the mobile infusion device during use, wherein the opening, the central chamber and the at least one roller have a length that is long enough to accommodate any size bag and in the standby mode the spring mechanism is recharged for future use.

The housing generally has a third portion shaped to define an upper chamber disposed above the central chamber, the upper chamber being shaped to receive an empty portion of the bag during use.

In at least some embodiments, a fourth portion of the housing is a cover that is removable to allow access to the central chamber.

In at least some embodiments, the housing has a fifth portion shaped to define a second opening in communication with the central chamber, the second opening being shaped to receive an emptied portion of the bag after it passes through the central chamber and allow the emptied portion of the bag to exit the device during use.

In at least some embodiments, the device comprises a handle located at an upper portion thereof to allow the device to be carried or moved during use.

In at least some embodiments, the user interface of the control mechanism is located near the handle to allow the user to hold and control the device using one hand.

In at least some embodiments, the bag is an Intravenous (IV) bag and the device further comprises a removable drip chamber holder having a first portion that is removably coupled to the housing and a second portion that is configured to releasably hold a drip chamber in a substantially vertical position.

In at least some embodiments that use an IV bag, the device further comprises an IV connector having an angled portion that has a first end that is coupled to an exit nozzle of the IV bag and a second end that is coupled to regular IV tubing for infusion to a patient.

In at least some embodiments, the device comprises a pressure applicator disposed within the central chamber and the at least one roller comprises a single roller in close proximity to the pressure applicator, the single roller and the pressure applicator being configured to apply pressure to the bag as the bag passes therebetween during use.

In at least some embodiments, the pressure applicator is one of a rod, a squeegee, a roller, or a constriction member having a slot with a width that is slightly larger than the thickness of the bag.

In at least some embodiments, the at least one roller comprises an attachment member to releasably attach to the bag during use.

In at least some embodiments, the at least one roller comprises one of a soft pliable outer surface and a non-smooth rough surface to improve grip on the bag during use.

In at least some embodiments, the housing comprises first and second endcaps disposed near opposite ends of the central chamber, the spring mechanism comprises a drive spring disposed within one of the endcaps and operatively coupled to a first end of the at least one roller to transmit a drive force thereto during use, and the user interface comprises a control button coupled to the drive spring and disposed near the endcap having the drive spring, the control button being configured to allow a user to start and stop rotation of the at least one roller.

In at least some embodiments, the housing comprises first and second endcaps disposed near opposite ends of the central chamber, the spring mechanism comprises a first drive spring disposed within the first endcap and a second drive spring disposed within the second endcap, the first and second drive springs being operatively coupled to opposite ends of the at least one roller to transmit a drive force thereto during use, and the user interface comprises at least one control button coupled to one of the drive springs and disposed near one of the endcaps, the at least one control button being configured to allow a user to start and stop rotation of the at least one roller.

In at least some embodiments, the device further comprises a stand that is removably coupled to a bottom portion of the housing.

In at least some embodiments, the device further comprises a first pair of legs that are removably coupled to the first end cap and a second pair of legs that are removably coupled to the second end cap, wherein the first and second pair of legs have legs that are pivotable between an open position to allow the device to stand and a closed position to allow the device to be carried and to form a protective frame for the device.

In at least some embodiments, the rotation assembly comprises first and second rollers disposed within the central chamber, having outer surfaces in close proximity to one another and configured to apply the force to the bag when the bag passes therebetween during use.

In at least some embodiments, the housing further comprises a first set of angled walls on a first side of the rollers defining an entry pathway for the bag between the rollers and a second set of angled walls on an opposite side of the rollers defining an exit pathway out of the rollers for the bag, the first and second set of angled walls also being configured to prevent the bag from coiling around the rollers.

In at least some embodiments, the rotation assembly further comprises a latch mechanism having a knob having a first engagement surface and a rotatable drive member having a first engagement surface, the drive member being operatively coupled to the spring mechanism and the first roller, the knob being movable between a first position in which the first and second engagement surfaces engage one another and the spring mechanism, the drive member and the at least one roller are operatively coupled and a second position in which the first and second engagement surfaces do not engage one another and the spring mechanism is configured to be recharged.

In at least some embodiments, the spring mechanism comprises a spool that is rotatably coupled to the housing and a drive spring having a first end coupled to the drive member and a second end coupled to the spool, wherein during start mode the drive spring is configured to coil around the spool thereby imparting a rotational drive force to the drive member which is translated to the first roller.

In at least some embodiments, the device further comprises a gearing mechanism having first and second gears that are operatively coupled to the first and second rollers respectively, and the first and second gears are operatively coupled to one another so that the drive force is transferred from the first roller to the second roller during the start mode.

In at least some embodiments, the control assembly is movable between a locked position and an unlocked position due to actuation of the user interface, wherein, during use, the at least one roller is allowed to rotate when the control assembly is in the unlocked position during the start mode and during the recharging of the spring mechanism and the at least one roller is prevented from rotating when the control assembly is in the locked position during the stop mode.

In at least some embodiments, the user interface of the control mechanism comprises a toggle switch, a slide-switch, a lever or at least one button.

In at least some embodiments, the spring mechanism comprises at least one spring that is a constant force spring, a clock spring, a self-coiling spring, a variable force spring, a conforce spring, a contorque spring, a torsion spring or a power spring.

In at least some embodiments, the device further comprises a rotatable crank that is operatively coupled to the at least one roller and the spring mechanism to allow a user to rotate the at least one roller in an opposite direction of a drive direction to remove the bag and to charge the spring mechanism.

In at least some embodiments, the control mechanism further comprises a latch mechanism that is movable between first and second positions during use due to actuation by a user and the control assembly is movable between first and second positions during use due to actuation of the user interface, wherein during use, the at least one roller is allowed to rotate when the control assembly and the latch mechanism are in the first position and the at least one roller is prevented from rotating when at least one of the control assembly and the latch mechanism is in the second position.

In another aspect, at least one embodiment described herein provides a mobile infusion device that does not use gravity to expel fluid from a bag, wherein the mobile infusion device comprises a housing including a first portion shaped to define a central chamber in the housing and a second portion shaped to define a first opening in the housing that is in communication with the central chamber and adapted to receive a portion of the bag during use; a rotation assembly coupled to the housing, the rotation assembly including at least one roller located within the central chamber, a drive member operatively coupled to the at least one roller, and a drive spring operatively coupled to the drive member, the drive spring and the drive member being configured to rotate the at least one roller in order to move the bag and apply a force to a portion of the bag to expel fluid from the bag during use; and a control mechanism operatively coupled to the rotation assembly, the control mechanism having a control assembly that can be actuated between an unlocked position and a locked position and a user interface for allowing a user to control the actuation of the control assembly, the control assembly allowing the drive member and the at least one roller to rotate or the drive spring to be recharged when the control assembly is in the unlocked position and the control assembly preventing rotation of the drive member and the at least one roller or recharging of the drive spring when the control assembly is in the locked position, wherein the opening, the central chamber and the at least one roller have a length that is long enough to accommodate bags of various sizes.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

For a better understanding of the various embodiments described herein and to show more clearly how these various embodiments may be carried into effect, reference will now be made, by way of example only, to the accompanying drawings which show at least one example embodiment and in which:

FIG. 5A is a front perspective view of another example embodiment of a mobile infusion device;

FIG. 5B is a cross-sectional view of the mobile infusion device of FIG. 5A in which an IV bag has been used and is nearly empty;

FIG. 5C is a cross-sectional view of an alternative embodiment of the mobile infusion device of FIG. 5A;

FIG. 10D is a front view of the mobile infusion device of FIG. 10A in which an IV bag has been partially used;

FIG. 10E is a cross-sectional side view of the mobile infusion device of FIG. 10A along the line A-A of FIG. 10D;

FIGS. 10L and 10M are magnified views of the portion H of the mobile infusion device of FIG. 10K showing a clutch or latch mechanism in engaged and disengaged positions, respectively;

FIGS. 10N and 10O are cross-sectional side views of the mobile infusion device of FIG. 10A along the line E-E of FIG. 10J showing the latch in engaged and disengaged positions, respectively.

DETAILED DESCRIPTION

Figure 1A:
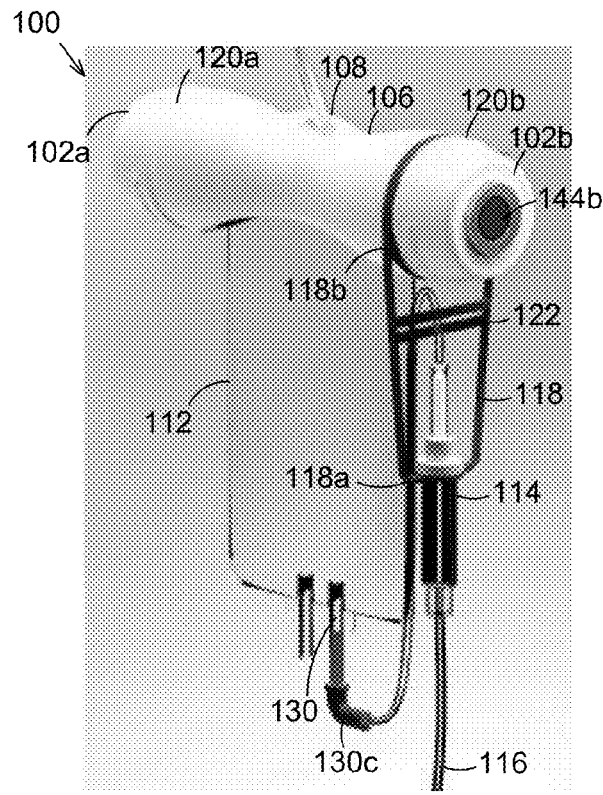
FIG. 1A is a perspective view of an example embodiment of a mobile infusion device.

Various devices or processes will be described below to provide an example of an embodiment of each claimed invention. No embodiment described below limits any claimed invention and any claimed invention may cover processes or devices that differ from those described below. The claimed inventions are not limited to devices or processes having all of the features of any one device or process described below or to features common to multiple or all of the devices or processes described below. It is possible that a device or process described below is not an embodiment of any claimed invention. Any invention disclosed in a device or process described below that is not claimed in this document may be the subject matter of another protective instrument, for example, a continuing patent application, and the applicant, inventor or owners do not intend to abandon, disclaim or dedicate to the public any such invention by its disclosure in this document.

Furthermore, it will be appreciated that numerous specific details are set forth in order to provide a thorough understanding of the various embodiments described herein. However, it will be understood by those of ordinary skill in the art that the various embodiments may be implemented without these specific details. In other instances, well-known methods, procedures and components have not been described in detail so as not to obscure the embodiments described herein. In addition, where considered appropriate, reference numerals may be repeated among the figures to indicate corresponding or analogous elements.

It should also be noted that the terms coupled or coupling as used herein can have several different meanings depending in the context in which these terms are used. For example, the terms coupled or coupling generally has a mechanical connotation and may indicate that two elements or devices can be physically connected to one another or connected to one another through one or more intermediate elements or devices via a physical element. In addition, when two objects are described herein as being in "close proximity" or being "proximal" to one another, it is meant to cover both cases in which there is a slight gap between the two objects or the two objects are in contact with one another.

It should be noted that terms of degree such as "substantially", "about" and "approximately" as used herein mean a reasonable amount of deviation of the modified term such that the end result is not significantly changed. These terms of degree should be construed as including a deviation of up to ±10% of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means up to plus or minus 10% of the number to which reference is being made.

Furthermore, in the following passages, different aspects of the embodiments are defined in more detail. Each aspect so defined may be combined with any other aspect or aspects unless clearly indicated to the contrary. In particular, any feature indicated as being preferred or advantageous may be combined with at least one other feature or features indicated as being preferred or advantageous.

Various embodiments are described herein for a mobile infusion device that applies a constant force to expel a liquid from any bag. Accordingly, although an IV bag is used extensively in this description, it should be understood that the mobile infusion devices described herein can be used to expel fluid from other types of bags which allows the various mobile infusion devices described herein to be used for a wide variety of applications ranging for use in hospitals, at home, in agriculture and irrigation, as well as in the military, emergency medical and rescue services as well as the aerospace fields. For example, some of the various mobile infusion devices described herein can be used by astronauts to infuse liquids or liquid food into their mouths while they are in outer space.

Referring now to FIG. 1A, shown therein is a perspective view of an example embodiment of a mobile infusion device 100. The mobile infusion device 100 comprises two endcaps 102a and 102b, a housing 106 and a central chamber 104 disposed within the housing 106. The mobile infusion device 100 may also comprise a handle 108, which may be optional in some cases. The mobile infusion device 100 may be attached to an IV pole, like a traditional IV bag, for purposes of illustration only, and when patient needs to be mobile, the mobile infusion device can be removed from the pole and carried on and mobilized by the patient. As will become apparent to a person of ordinary skill in the art, the mobile infusion device 100 can be used in a variety of ways such as, but not limited to, being carried by an ambulatory patient using any suitable means, such as the hands of a patient, medical practitioner or caregiver, a harness, a belt, a clip, a strap, a backpack or other carrying case, and the like, for example. The mobile infusion device 100 may also be attached to a wheelchair, hospital bed, gurney or a custom-made mini-pole, as is shown in FIGS. 3A-3G, for example.

An IV bag 112, containing the fluid to be delivered to a patient, is attached to the mobile infusion device 100. In this example embodiment, the IV bag 112 is a traditional IV bag commonly used by IV infusion therapy providers. The size of the mobile infusion device 100 can be configured to support different IV bags 112 having different sizes, whether they are standard or custom sizes.

The mobile infusion device 100 infuses or expels fluids from the IV bag 112 to a drip chamber 114. In this example embodiment, the drip chamber 114 is cylindrical, however, other shapes may be employed depending on how and where the mobile infusion device 100 is to be used. For example, the drip chamber 114 may be spherical in shape. The drip chamber 114 infuses fluids to the patient via an IV line 116 as is standard in the art.

It should also be noted that the various mobile infusion devices described herein can be used to expel liquids out of an IV bag regardless of whether a drip chamber is used with the IV bag. Accordingly, the existence of a drip chamber is not a precondition for infusing liquids to the patient using the mobile infusion devices described herein, since infusion can occur through any means that are connected to the fluid exit side/tubing of the IV bag 112.

The mobile infusion device 100 may further include a drip chamber holder 118 that is coupled to the housing 106 of the mobile infusion device 100 (although in some cases the drip chamber holder 118 can be optional). In general, the drip chamber holder 118 has a first portion that releasably engages the drip chamber 114 and a second portion that releasably engages the housing 106 of the mobile infusion device 100. Furthermore, the drip chamber holder 118 is generally configured to rotate freely about a horizontal axis to maintain the drip chamber 114 in a substantially vertical position. The drip chamber holder 118 improves the safety and convenience of the mobile infusion device 100 since it allows the cylindrical drip chamber to be maintained in an upright position and also to avoid the obstruction of the tubing line.

In this example embodiment, the first portion of the drip chamber holder 118 comprises a horizontally oriented loop 118a that substantially forms a friction fit around the circumference of a portion of the drip chamber 114. The second portion of the drip chamber 118 comprises a loop 118b that fits within a groove or channel 120a or 120b on an outer upper surface of the housing 106 of the mobile infusion device 100. The grooves 120a and 120b are deep enough to hold the loop 118b in place when in use. The grooves 120a and 120b can be located near an end portion of both ends of the housing 106. Accordingly, there can be one or two grooves so that the drip chamber holder 118 can be placed near the right or left side of the mobile infusion device 100. In alternative embodiments, there may only be one groove 120a or 120b. In addition, in alternative embodiments there can be a bearing that is mounted in the grooves 120a and 120b to achieve a tighter fit with the drip chamber holder 118 to further aid in maintaining the drip chamber 114 in a vertical orientation which is important for safety reasons. The drip chamber holder 118 further comprises at least one horizontal member 122 to provide structural stability so that the drip chamber 114 is relatively stationary during use.

It should be noted that the mobile infusion device 100 further includes an IV connector 130c when the drip chamber holder 118 is used. The IV connector 130c has a 90 degree angled portion 130c that has a first end that is coupled to the exit nozzle 130 of the IV bag 112 and a second end that is coupled to regular IV tubing. The horizontal member 122 of the drip chamber holder 118 is configured to receive and hold a portion of the IV tubing coming from the IV connector 130c during use. The IV connector 130c is used to avoid bending of the IV line and thus prevent flow obstruction during use. In some embodiments, depending on the application and user needs, a spherical drip chamber is used for safety reasons, i.e. to prevent air bubbles from entering the IV tubing.

The mobile infusion device 100 also comprises a pair of control buttons 144a and 144b that are used to enable specific functions, such as starting, stopping and resetting a rotation assembly of the mobile infusion device 100. The rotation assembly can be actuated by pressing the control button 144a, which causes the IV bag 112 to be pulled up and a substantially constant force to be applied to the IV bag 112 to cause fluid within the IV bag 112 to be dispelled through the nozzle 130 towards the drip chamber 114 and then the IV line 116. The rotation assembly can be stopped by pressing the same control button 144a which stops the IV bag 112 from being pulled up by the mobile infusion device 100. The control button 144a can then be pressed again to restart the rotation assembly. The control button 144b is pressed when it is desired to eject the IV bag 112 (i.e. remove the IV bag 112 from the mobile infusion device 100) and to place the rotation assembly in a starting position so that another IV bag can be loaded and used by the mobile infusion device 100. Accordingly, the mobile infusion device 100 is configured to have various modes or operation including a start mode, a stop mode, and a standby mode (in which the drive spring(s) used in the rotation assembly are reloaded or recharged for subsequent use with another IV bag 112).

It should be noted that for some of the various mobile infusion device embodiments described herein, it is possible to manually remove the IV bag 112 by grabbing a bottom portion of the IV bag 112 and pulling it down until the top portion of the IV bag 112 is clear of the roller(s).

It should be noted that during use, a force is applied to the IV bag 112 to expel fluid from the IV bag 112 so that gravity is not relied upon to expel the fluid as is done in conventional IV poles. This provides several advantages such as not requiring the IV bag 112 to be placed at a certain minimum height above the site where the IV line 116 is inserted into the patient. This allows the mobile infusion device 100 to be used in a variety of situations, environments, heights and positions, some of which are shown in FIGS. 1D and 3A to 3G; this is generally not possible with conventional IV poles.

Figure 1B:
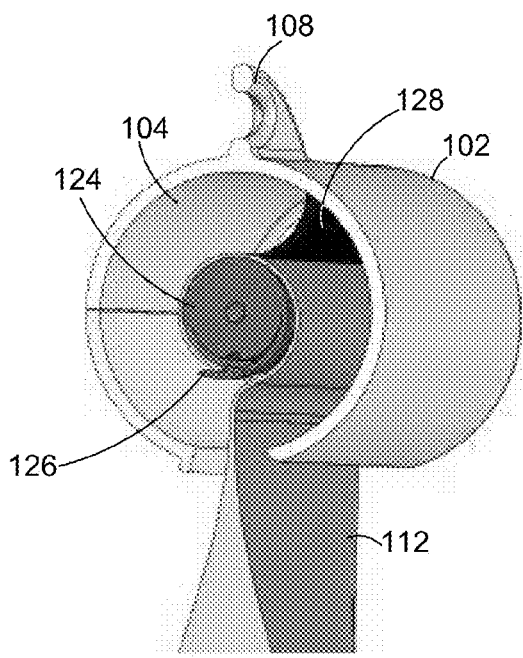
FIG. 1B is a perspective cross-sectional view of a portion of the mobile infusion device of FIG. 1A.

Referring now to FIG. 1B, shown therein is a perspective cross-sectional view of a portion of the mobile infusion device 100. It can be seen that the mobile infusion device 100 further comprises a drum or roller 124 that is part of the rotation assembly and extends across the longitudinal axis of the central chamber 104 and has an attachment member 126 that is used to releasably attach to the IV bag 112. In this example embodiment, the attachment member 126 is a hook that can engage a loop on the top of the IV bag 112. The roller 124 is part of the rotation assembly and is configured such that it can rotate about its shaft (e.g. along its longitudinal axis) during use due to the action of a spring-based actuator in the rotation assembly, an example of which is described in further detail with respect to FIG. 2E. Other parts of the rotation assembly are described in relation to FIGS. 2A-2C and 2E.

The mobile infusion device 100 further comprises a pressure applicator 126 that is located within the central chamber 104 and is disposed adjacent to the roller 124. In some implementations the pressure applicator 126 can be in contact with the roller 124 but is slightly movable as the IV bag 112 passes therebetween. In other implementations there can be a small gap between the pressure applicator 126 and the roller 124. In this example embodiment, the pressure applicator 126 is a squeegee but in other implementations the pressure applicator 126 can be other elements such as, but not limited to, a rod, a roller, a constriction member having a slot with a width that is slightly larger than the thickness of the IV bag 112 and the like, for example.

In use, the IV bag 112 is connected to the roller 124 and as the roller 124 turns the IV bag 112 wraps around the roller 124. As the IV bag 112 wraps around the roller 124, it passes between the roller 124 and the pressure applicator 126 which applies a sufficient amount of pressure to expel fluid contained within the IV bag 112 through the nozzle 130 and the IV connector 130c to the drip chamber 114 and then to the IV line 116.

Figures 1C, 1D:
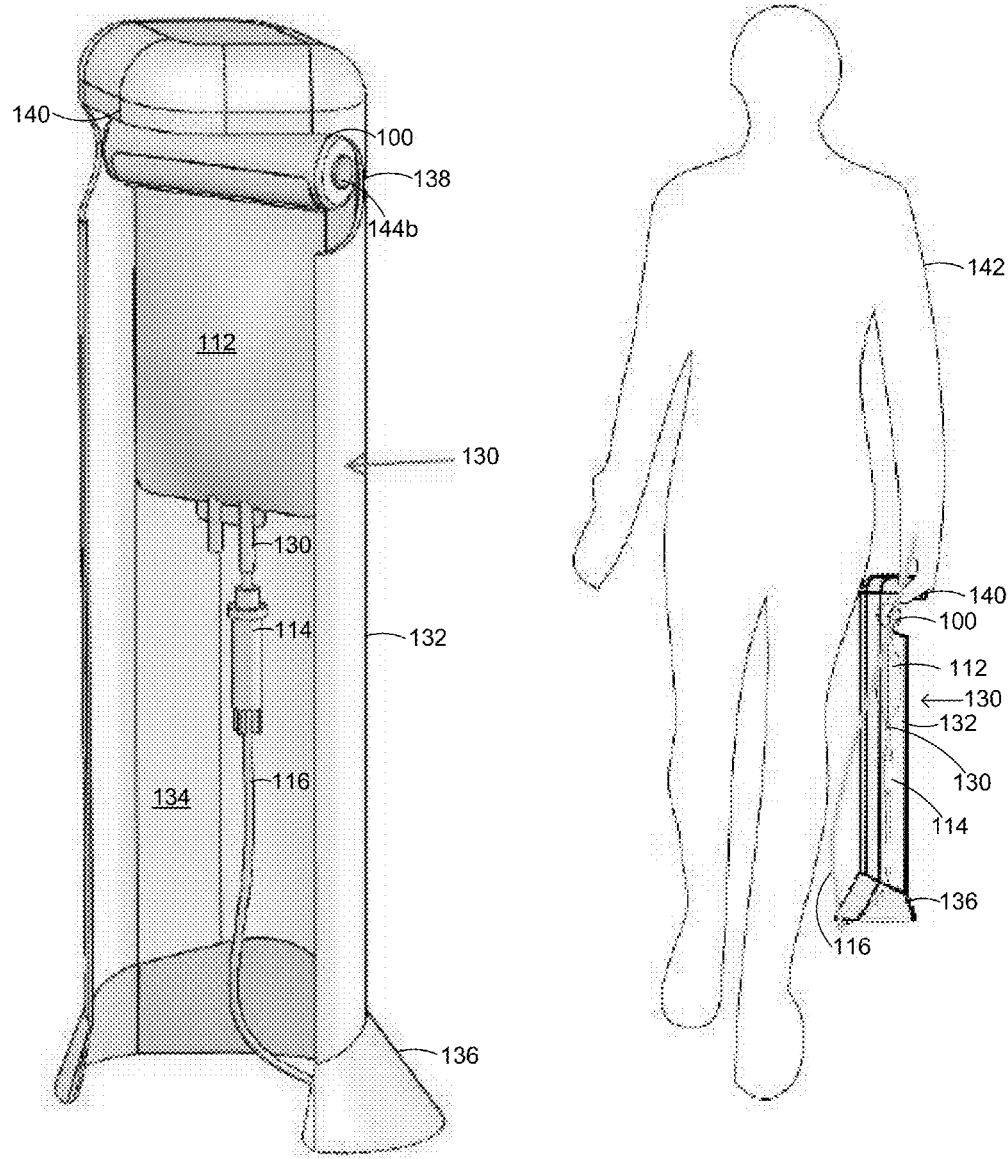
FIG. 1C is a perspective view of a portable carrier that can be used with the mobile infusion device of FIG. 1A.
FIG. 1D is an illustration showing an example of a patient carrying the mobile infusion device of FIG. 1A via the portable carrier of FIG. 1C.

Referring now to FIG. 1C, shown therein is a perspective view of a portable carrier or carrying case 130 that can be used with the mobile infusion device 100. The portable carrier 130 is configured to maintain the IV bag 112 and the drip chamber 114 in a substantially vertical position as well as allow for easy visual inspection of these elements; this can allow for a visual inspection of how much fluid is left in the IV bag 112.

The portable carrier 130 comprises a housing 132 having an inner chamber 134, a base 136, a holder 138 and a handle 140. In general, the housing 132 does not extend around the entire circumference of the portable carrier 130 but rather includes a vertical opening to allow the mobile infusion device 100 along with the IV bag 112 to be easily inserted and removed from the portable carrier 130 by releasably attaching the mobile infusion device 100 to the holder 138.

The holder 138 is used to hold the mobile infusion device 100 in place during operation. The holder 138 can be shoulders or a ledge that is formed from a portion of the housing 132. Alternatively, the holder 138 can be hooks or loops that are attached to an inner portion of the housing 138 and are shaped to releasably engage the outer surface of the mobile infusion device 100. The holder 138 is shaped to allow the patient, a medical practitioner or another individual such as a caregiver easy access to the endcaps 102a and 102b of the mobile infusion device 100 which provide special functionality as will be described with relation to FIGS. 2A to 2E.

The base 136 of the portable carrier 130 allows the portable carrier 130 to be placed on a flat surface during use. In this example embodiment, the base 136 has a conical shape that flares out from the main body of the housing 132 in order to provide increased stability when the portable carrier 130 is placed on a surface. In an alternative embodiment, the base 136 can extend along the entire circumference of the housing 132. In another embodiment, the base 136 can have a solid bottom wall or an annular ring to provide further stability for the portable carrier 130 during use. In another embodiment, the base 136 can have a channel or aperture through which the IV line 116 can pass for connection to the patient.

The handle 140 allows a patient to hold the portable carrier 130 during use or allow someone to hold the portable carrier 130 when transporting the portable carrier 130. In this example embodiment, the handle 140 is a top portion of the housing 132 that extends away from the housing 132 and has a lip or groove that a patient can hold onto with their fingers. In an alternative embodiment, the handle 140 can be vertically disposed at the top of the housing 132 and be in the form of a loop that is integrally formed with the housing 132 or is a separate piece that is pivotally coupled to the housing 132.

Referring now to FIG. 1D, shown therein is an example of a patient 142 carrying the mobile infusion device 100 via the portable carrier 130. The patient 142 grips the handle 140 of the portable carrier 130 to carry the mobile infusion device 100 as the patient walks to a certain destination or exercises. In addition, the portable carrier 130 can be used instead of a conventional IV pole. Since the mobile infusion device 100 provides a force to expel the fluid from the IV bag 112 instead of relying on gravity, the mobile infusion device 100 does not have to be maintained at the heights used for conventional IV poles, which allows the mobile infusion device 100 to be used at a lower height in the carrier 130.

Figure 2A:
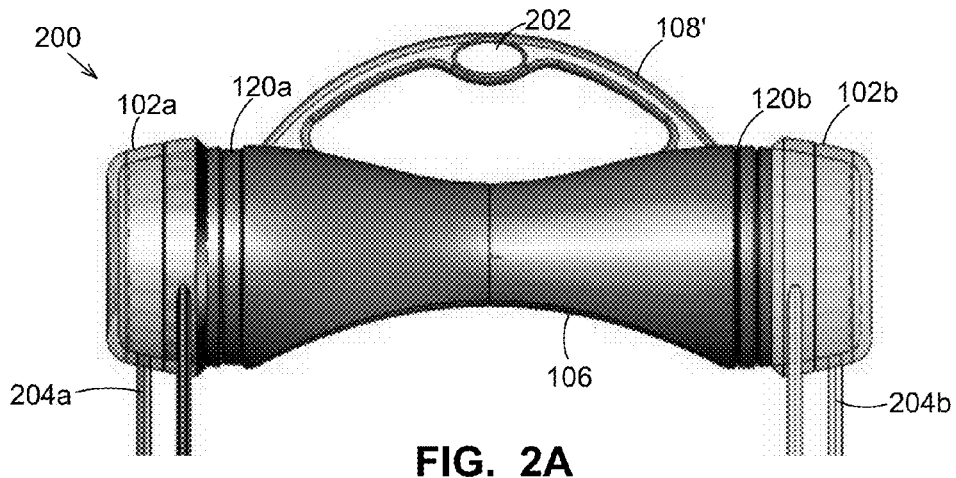
FIG. 2A is a front view of a portion of another example embodiment of a mobile infusion device.

Referring now to FIG. 2A, shown therein is front view of a portion of another example embodiment of a mobile infusion device 200. The mobile infusion device 200 has a handle 108' that is wider than the handle 108 of the mobile infusion device 100 making it easier for a patient or a health care practitioner to grab or carry the mobile infusion device 200. The handle 108' also comprises an aperture 202 that can be used to hook onto another object such as, but not limited to, an IV pole, for example. The mobile infusion device 200 further comprises a pair of detachable legs 204a and 204b that form a mini-stand which can be used to support the mobile infusion device 200 so that it does not have to be hung from an IV pole. It can be seen that the mobile infusion device 200 is similar to the mobile infusion device 100 but has the addition of the pairs of legs 204a and 204b and some differently shaped components. The mobile infusion device 200 also comprises a ring 206 located near the halfway point of the housing 106 to provide additional structural strength to the housing 106.

Figure 2B:
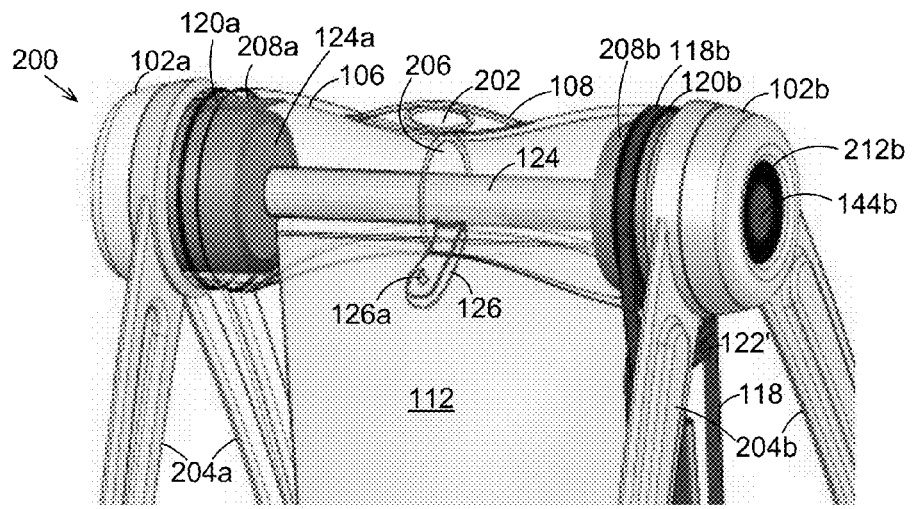
FIGS. 2B and 2C are perspective views of a portion of the mobile infusion device of FIG. 2A with a portion thereof being transparent.
Figure 2C:
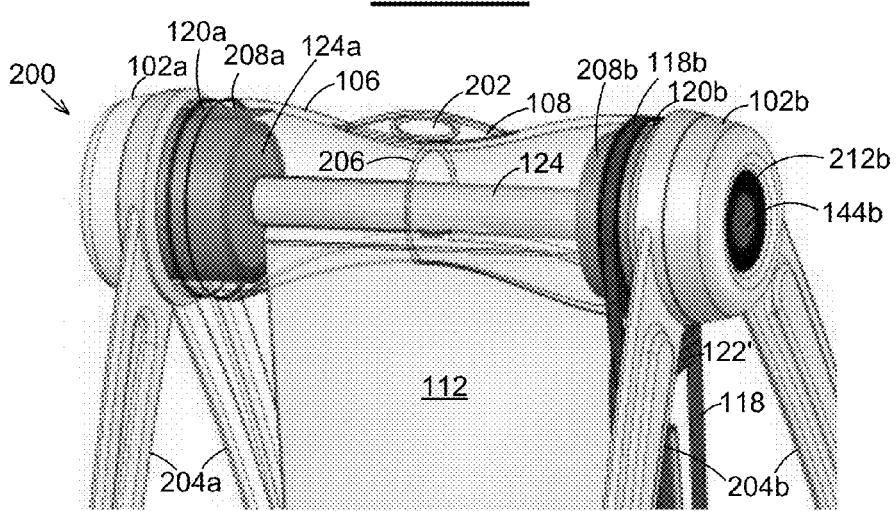

Referring now to FIGS. 2B and 2C, shown therein are perspective views of a portion of the mobile infusion device 200 with a portion of the housing 106 being transparent. In FIG. 2B, the attachment member 126 is in an open position ready to engage a loop or an aperture at the top of the IV bag 112 and in FIG. 2C, the attachment member 126 has engaged the top portion of the IV bag 112 and is in a closed position to secure the IV bag 112 to the roller 124. In this example embodiment, the attachment member 126 is a latch with a protrusion 126a that engages a complimentary shaped depression on the surface of the roller 124 to form a snap-fit when in the closed position. In alternative embodiments, the attachment member 126 can be a hook.

In FIGS. 2B and 2C, the pairs of legs 204a and 204b are both in an open position to provide the mobile infusion device 100 with a free-standing, stable structure. Alternatively, the pair of legs 204a and 204b can be moved to a closed position which allows the mobile infusion device 200 to be carried by the patient 142, a medical practitioner or another individual such as a caregiver, for example. The control buttons 212a and 212b can be pressed to actuate and rotate the legs 204a1 and 204a2 as well as 204b1 and 204b2 of each pair of legs 204a and 204b, respectively, to configure the pair of legs 204a and 204b in a closed position, an open position or at various intermediate positions between the open and closed positions.

In FIGS. 2B and 2C, the drip chamber holder 118 is also shown in which the horizontal member 122' is located closer to the end portion 118b so that it fits more snugly around the housing 106 of the mobile infusion device 200 to provide greater stability in order to reduce movement of the drip chamber 114 during use. The drip chamber holder 118 can be slid over one of the pair of legs 204a or 204b (depending on which side the drip chamber holder 118 is being placed) when the pair of legs 204a and 204b are in a closed position and onto the housing 106 of the mobile infusion device 200 to engage the groove 120a or 120b.

Figure 2D:
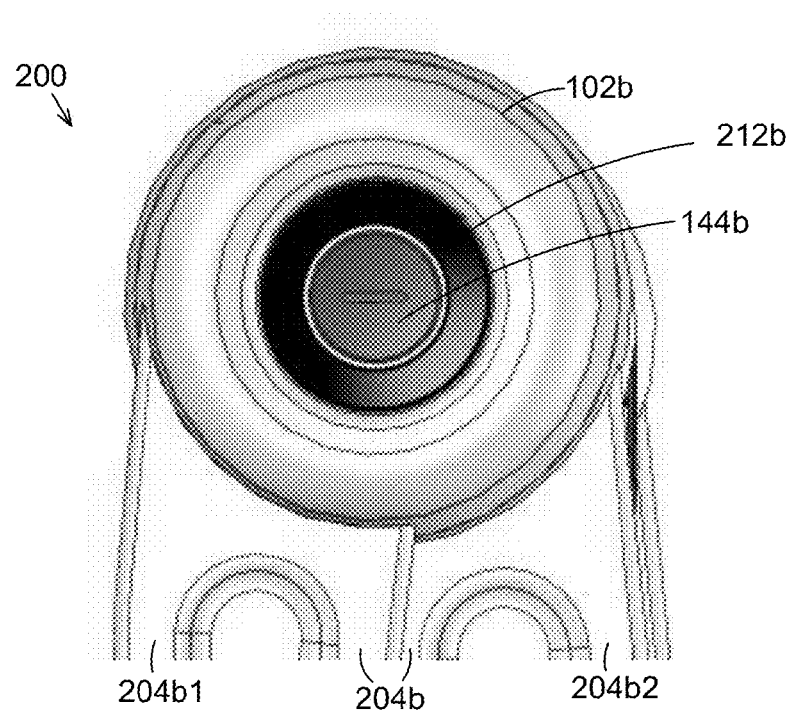
FIG. 2D is a side view of a portion of the mobile infusion device of FIG. 2A.

Referring now to FIG. 2D, shown therein is a side view of a portion of the mobile infusion device 200. It can be seen that the pair of legs 204b each have grooves or channels 204b1 and 204b2 which reduces the amount of material used for the pair of legs 204b by a certain amount to decrease the weight of the mobile infusion device 200 while not compromising the structural integrity and the stability of the pair of legs 204b. Similar grooves or channels can be used for the pair of legs 204a.

Figure 2E:
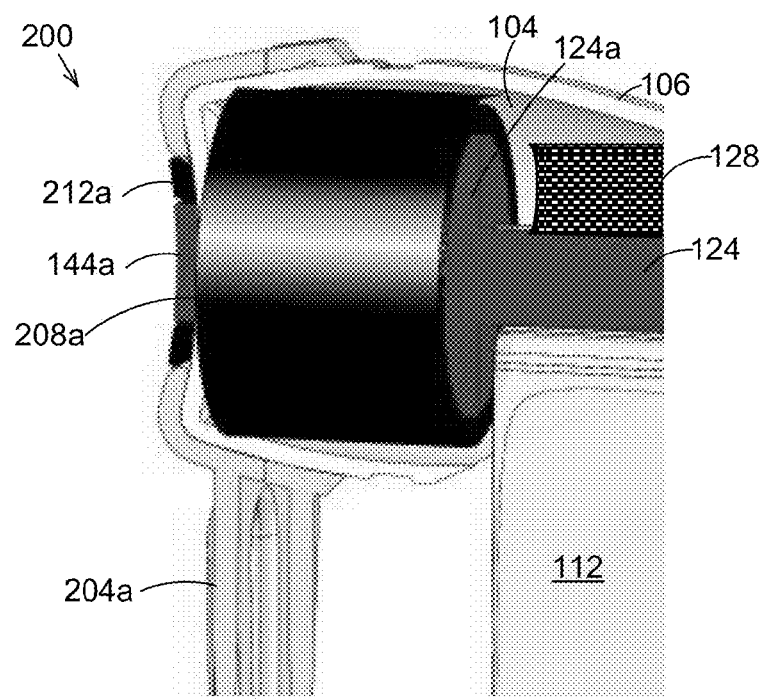
FIG. 2E is a front view of a portion of the mobile infusion device of FIG. 2A with a portion of the housing removed.

Referring now to FIG. 2E, shown therein is a front view of a portion of the mobile infusion device 200 with a portion of the housing 106 removed. Each of the endcaps 102a and 102b includes a control button 144a and 144b, respectively. The control buttons 144a and 144b are spring actuated in this example embodiment but other forms of actuation may be used in alternative embodiments such as, but not limited to, a toggle switch, a slide switch, a lever, a knob, and the like, for example.

The central chamber 104 includes the roller 124, a pair of drive springs 208, a squeegee 128, and a bottom opening 210. In this example embodiment, the springs 208 are constant force springs. However, in alternative embodiments, other types of springs can be used such as, but not limited to, clock springs, self-coiling springs, variable force springs, conforce and contorque springs, and power springs, for example. The bottom opening 210 extends along a substantial portion of the length of the central chamber 104. The length of the bottom opening 210 is selected to be greater than the largest width of the IV bag 112 for which the mobile infusion device 200 is configured to operate with.

As was mentioned for the mobile infusion device 100, the squeegee 128 is one form of a pressure applicator and in alternative embodiments other objects can be used to assert pressure on the IV bag 112 during operation such as, but not limited to, a rod, a roller, a cable, a constriction member having a slot with a width that is slightly larger than the thickness of the IV bag 112 and the like, for example. The squeegee 128 is positioned across the length of the central chamber 104 such that it is substantially parallel to the roller 124 and in contact therewith or slightly spaced apart from the roller 124.

The roller 124 is positioned across the length of the central chamber 104 and is configured to rotate about its longitudinal axis under force from the springs 208a and 208b. Using two drive springs provides enhanced power and torque for moving and squeezing heavier bags of up to 5 L, for example, which is currently the largest IV bag used today. The roller 124 is further operatively coupled with each of the endcaps 102, as will be described.

Each of the springs 208a and 208b are part of the rotation assembly and are positioned at distal ends of the roller 124 and attached to enlarged ends 124a of the shaft upon which the roller 124 is mounted. The enlarged ends 124a reduce the amount of space between the springs 208 and an inner portion of the housing 106 so that the springs generally remain tightly coiled. Furthermore, the enlarged ends 210 allow for upper and lower gaps above and below the roller 124 within the central chamber 104. These upper and lower gaps are sized to receive the empty portion of the IV bag 112 as it is pulled up by the roller 124 and coils around the roller 124.

The springs 208a and 208b are made of a certain type of material and are shaped such that they generate sufficient pressure to expel fluid from the IV bag 112 and pull the IV bag 112 up into the central chamber 104 of the mobile infusion device 200 and minimizing the impact on the drip rate caused by changing the heights of the IV bag 112 in various usage scenarios for the mobile infusion device 200 and especially compared to the height of conventional IV poles. For example, there can be embodiments in which the springs 208a and 208b are designed to provide approximately 150 to 200 N of force. However, the location, number and the amount of force provided by the springs 208a and 208b may vary depending on the particular application of the mobile infusion device 200. For example, there can be some embodiments where only one drive spring is used that has the same strength as that of two drive springs; this reduces the size, weight and cost of the mobile infusion device. The selection of the type of drive spring may also depend on the particular application of the mobile infusion device. Furthermore, the material used to make the drive spring(s) may also vary.

In at least one embodiment, a portion of the housing 106 is movable or removable thereby operating as a cover that can be opened and closed to provide better access to the interior of the central chamber 104. The cover can be opened, for example, when attaching the IV bag 112 to the roller 124 or removing the IV bag 112 from the roller 124 or for servicing the mobile infusion device 200. There can also be embodiments in which there is no removable cover and the bottom opening is used for inserting and removing the IV bags 112.

The mobile infusion device 200 further comprises a latch mechanism (not shown) that is used to maintain tension on the springs 208 once they are wound. In this example embodiment, the latch mechanism is controlled by one of the control buttons 144a and 144b. However, in alternative embodiments, the latch mechanism may be located in a different area and/or controlled by a different mechanism. The control buttons 144a and 144b act as start and stop buttons on both sides of the mobile infusion device 200. Accordingly, pressing either the control button 144a and 144b can start or stop the operation of the mobile infusion device 200. In alternative embodiments, separate buttons can be used to respectively start and stop the operation of the mobile infusion device 200.

Operation of the mobile infusion device 200 is described as follows (the mobile infusion device 100 operates in a similar manner). A full IV bag 112 is attached to the mobile infusion device 200 by lifting the cover and attaching a loop on the upper portion of the IV bag 112 onto the attachment member 126 of the roller 124. In embodiments where there is no removable cover, the roller 124 can be rotated such that the attachment member 126 is located near and facing the bottom opening 210. The IV bag 112 is then brought to a starting point, or standby position, by rotating the roller 124 so that the liquid level in the IV bag 112 is near or at the bottom opening 210 of the housing 106. Rotation of the roller 124 is then started by pressing one of the control buttons 144a and 144b that unlatches the springs 208. Providing these buttons on both sides of the mobile infusion device 200 provides more flexibility of use and operation. Once the springs 208 are unlatched they cause the roller 124 to rotate about its longitudinal axis. Rotation of the roller 124 causes the IV bag 112 to be slowly drawn into the central chamber 104 and to wrap around the roller 124. As the IV bag 112 passes between the roller 124 and the pressure applicator 128, a suitable amount of force or pressure is applied to the fluid in the IV bag 112, thus expelling the fluid from the IV bag 112 into the drip chamber 114 and then into the IV line 116. Accordingly, the mobile infusion device 200 is independent of gravity for operation which allows the mobile infusion device 200 to be used in a variety of locations and heights, which is not possible with conventional IV poles since they rely solely on gravity for operation.

Operation of the mobile infusion device 200 can be stopped and resumed at any time by pressing the control button 144a or 144b to selectively engage and disengage the latch mechanism. Once the operation of the mobile infusion device 200 has stopped, whether it is because the IV bag 112 is empty or it was actively stopped on purpose, the IV bag 112 can be removed by pulling it out in continuous motion until it is mostly outside of the mobile infusion device 200 at which point it can be disengaged from the attachment member 126. Depending on the configuration of the attachment member 126, and the implementation of the mobile infusion device 200, it may be necessary to open the cover to completely remove the IV bag 112 or the IV bag 112 may automatically be removed when it is pulled out in a continuous motion.

During the IV bag release process, the springs 208 are automatically recharged and the latch mechanism is then engaged to maintain the required tension on the springs 208 so that the mobile infusion device 200 is ready for the next use. For example, pressing the stop button 144b locks the springs 208a and 208b. Pressing or activating a latch/clutch actuator then disengages the springs 208a and 208b from the shaft portions 208a and 208b, respectively. Now the IV bag release process is feasible and easier since there is no resistance from the springs 208a and 208b, and only the roller 124 which is mounted on the shaft rotates freely as the IV bag 112 is pulled out. Gearing combination at a particular rotational ratio to minimize the resistance to the springs and that are connected to the roller, although not shown in this embodiment, enable the auto recharge of the springs as the bag is pulled out. Once the IV bag 112 is pulled out a new IV bag can be inserted. The release button can be pressed again to enter the standby mode and engage the springs 208a and 208b to the shaft portions 128a and 128b of the roller 124 and may also turn the roller 124, such as a half turn for example, which is enough to bring the IV bag 112 to the standby position where the top of the fluid in the IV bag 112 is just below the bottom edge of the roller 124.

In an alternative embodiment, a bag release mechanism can be used to temporarily disconnect the roller 124 from the torsion springs 208 as explained previously. The bag release mechanism is activated by pressing a bag release button (not shown) or other suitable mechanism on the mobile infusion device 200. This will allow the IV bag 112 to more easily be removed, since there is no resistance provided from the springs 208a and 208b. However, this embodiment requires additional activity to recharge the springs 208a and 208b. For example, a crank or retractable/refoldable handle can be provided near one of the endcaps 102a or 102b which is then rotated to recharge or reload the springs 208a and 208b as described previously.

Figure 2F:
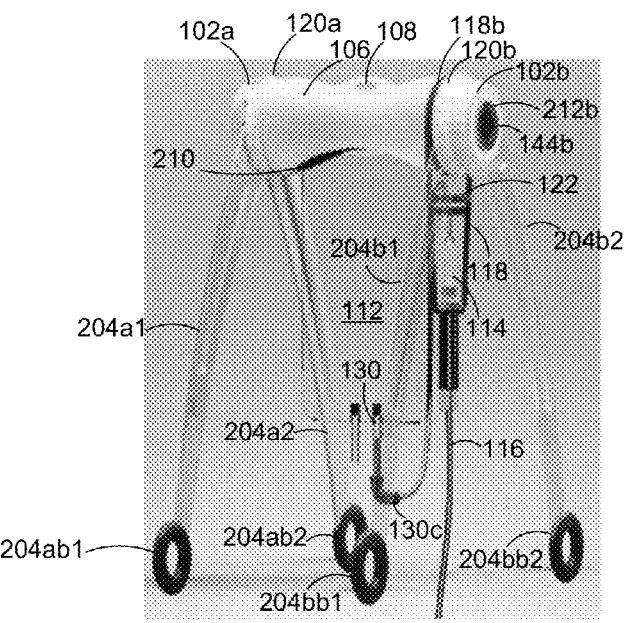
FIGS. 2F to 2G are perspective views of the mobile infusion device of FIG. 2A with a mini-stand in an open and closed position respectively.
Figure 2G:
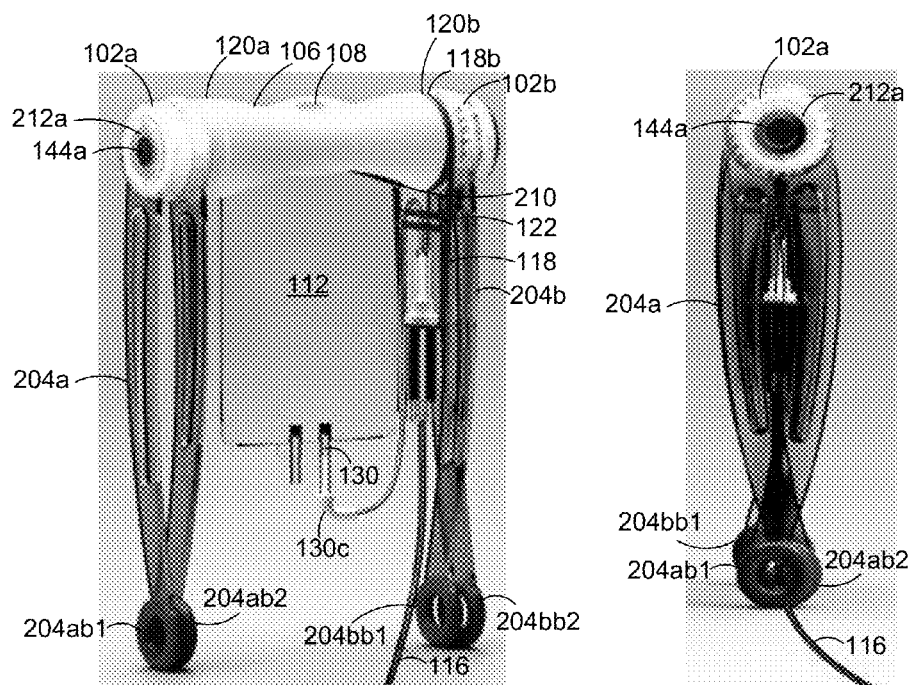

Referring now to FIGS. 2F to 2G, shown therein are perspective views of the mobile infusion device 200 with the pairs of legs 204a and 204b open in a mini-stand or standing configuration and closed in a carrying configuration, respectively. The pairs of legs 204a and 204b are each configured to movably connect to a corresponding one of the endcaps 102a and 102b of the mobile infusion device 200. The pair of legs 204a comprises two convex legs 204a1 and 204a2 with at least one generally convex outer surface and the pair of legs 204b comprise two convex legs 204b1 and 204b2 with at least one generally convex outer surface. Each of the pair of legs 204a and 204b couple about a pivot point at each endcap 102a and 102b. The legs 204a1, 204a2, 204b1 and 204b2 respectively comprise base members 204ab1, 204ab2, 204bb1 and 204bb2 that are used to support the legs on a surface so that the mobile infusion device 200 as a mini-stand apparatus. In this example embodiment, the base members 204ab1, 204ab2, 204bb1 and 204bb2 have a circular shape but in alternative embodiments they can have different shapes such as rectangular, square, triangular, pyramidal, conical, and the like. The mobile infusion device 200 can be used in a mini-stand configuration because it uses force to expel fluid from the IV bag 112 rather than to rely solely on gravity.

Figure 2H:
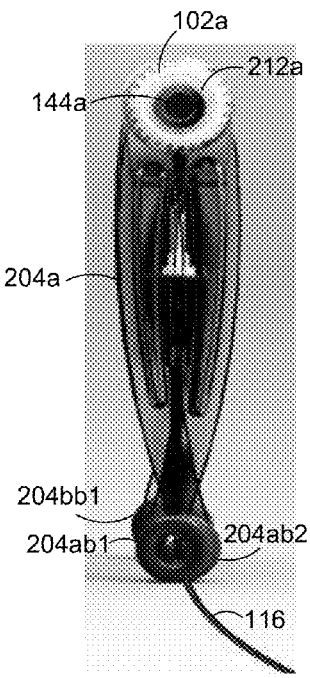
FIG. 2H is a side view of the mobile infusion device of FIG. 2A with the mini-stand in a closed position.

Referring now to FIG. 2H, shown therein is a side view of the mobile infusion device 200 with the pairs of legs 204a and 204b closed in the carrying configuration. The legs 204a1, 204a2, 204b1 and 204b2 have been rotated or pivoted so that their ends (i.e. bases 204ab1, 204ab2, 204bb1 and 204bb2) that are distal from the pivot point at the endcaps 102a and 102b are spaced together. The bases 204ab1 and 204ab2 can be aligned with one another or slightly offset from one another. Likewise, the bases 204bb1 and 204bb2 can be aligned with one another or slightly offset from one another. As can be seen, the convex curvature of the legs 204a1, 204a2, 204b1 and 204b2 provides a protective frame for the IV bag 112 when the mobile infusion device 200 is being carried since the outer edges of the legs 204a1, 204a2, 204b1 and 204b2 extends beyond the front and back of the IV bag 112. The protective frame reduces the risk of accidentally applying too much pressure to the IV bag 112 as a result of a collision or a fall.

In an alternative embodiment, another option to protect the IV bag 112 from getting damaged or ruptured, depending on the environment and conditions it is used in, is to use a clear transparent semi-rigid plastic container that can be connected to the housing 106 and that can hold the IV bag 112 in a desired position, and has a transparent portion, aperture or may be totally transparent to allow the liquid level of the IV bag 112 to be monitored. This plastic container can be used as a protective shield for IV bags when they are used especially in the outdoors or harsh environments. The transparent container can be attached and detached from the housing 106 allowing for increased flexibility of use and operation.

Figure 2I:
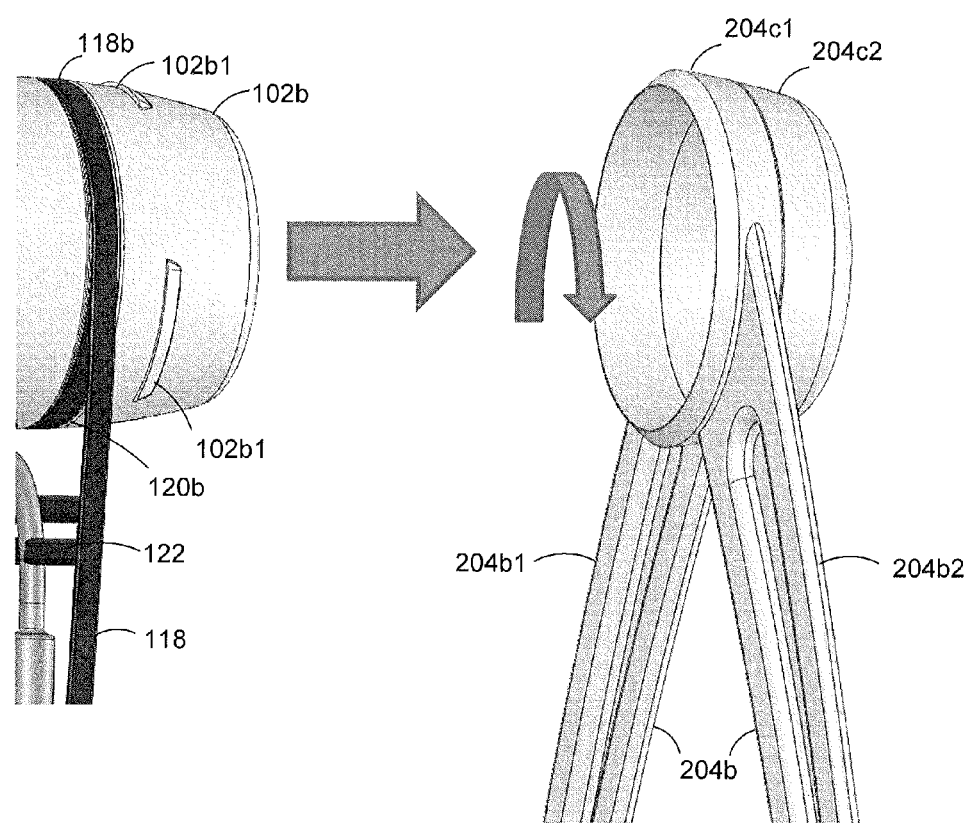
FIG. 2I is a side view of a pair of legs being rotatably coupled to an endcap of the mobile infusion device of FIG. 2A.

Referring now to FIG. 2I, shown therein is an illustration of how the legs 204b1 and 204b2 can be rotatably coupled to an endcap 102b of the mobile infusion device 200. The legs 204b1 and 204b2 are coupled to one another via first and second coupling members 204c1 and 204c2 that rotatably engage one another. The first coupling member 204c1 is part of the leg 204b2 and has an annual ring or annular ridge (not shown) that fits within an annular ring (not shown) at the edge of the second coupling member 204c2 which is part of the leg 204b1. The first and second coupling members 204c1 and 204c2 engage one another such that the legs 204b1 and 204b2 can be pivoted with respect to one another. In an alternative embodiment, the annular ring of the first coupling member 204c1 can have an annular shoulder on an outer portion thereof which extends around its circumference and the annular ring of the second coupling member 204c2 can have an annular groove on an inner portion thereof which extends around its circumference and is shaped to receive the lip of the first coupling member 204c1 to improve the stability of coupling between the first and second coupling members 204c1 and 204c2 while allowing them to pivot with respect to one another.

The first coupling member 204c1 also has grooves or ridges (not shown) on an inner portion thereof which faces the endcap 102b. The endcap 102b has ridges 102b1 (only two are shown for simplicity of illustration and there may be more in some embodiments). The grooves or ridges of the first coupling member 204c1 engage the ridges 102b1 to couple the pair of legs 204b to the endcap 102b. To do this, the first coupling member 204c1 is rotated slightly so that it can be received on the outer surface of the endcap 102b. The first coupling member 204c1 is then rotated so that the grooves or ridges of the first coupling member 204c1 proximal to the endcap 102b engage with the ridges 102b1 of the endcap 102b thus releasably fastening the pair of legs 204b to the endcap 102b. To remove the pair of legs 204b from the endcap 102b, the first coupling member 204c1 is rotated in the opposite direction so that the grooves or ridges of the first coupling member 204c1 no longer engage the ridges 102b1 which allows the first coupling member 204c1 to be slid off of the endcap 102b. Similar structure and action is used to couple the pair of legs 204a with the endcap 102a.

In an example embodiment, the mobile infusion device 200 can be designed so that its height (measured from the bottom of a given base to the top of the housing 102) can be about 12 inches and its width (measured from an outer surface of one pair of legs to the outer surface of the other pair of legs) can be about 8.5 inches. This allows the mobile infusion device 200 to accommodate larger size IV bags such as 500 mL and 1000 mL IV bags.

In another example embodiment, the mobile infusion device 200 can be designed so that its height can be about 10 inches and its width can be about 5.5 inches. This allows the mobile infusion device 200 to accommodate smaller size IV bags such as 100 mL and 250 mL IV bags.

It should be noted that the size of the dimensions of the mobile infusion device 200 given in these two examples are approximate and serve only as two examples of the sizes that can be chosen for the mobile infusion device 200. In other embodiments, which may depend on the intended purpose, other sizes can be chosen for the dimensions of the mobile infusion device 200 in order to accommodate smaller IV bag sizes or larger IV bag sizes up to 5000 ml or more, or anywhere between 250 ml to 5000 ml, for example.

Figure 3A:
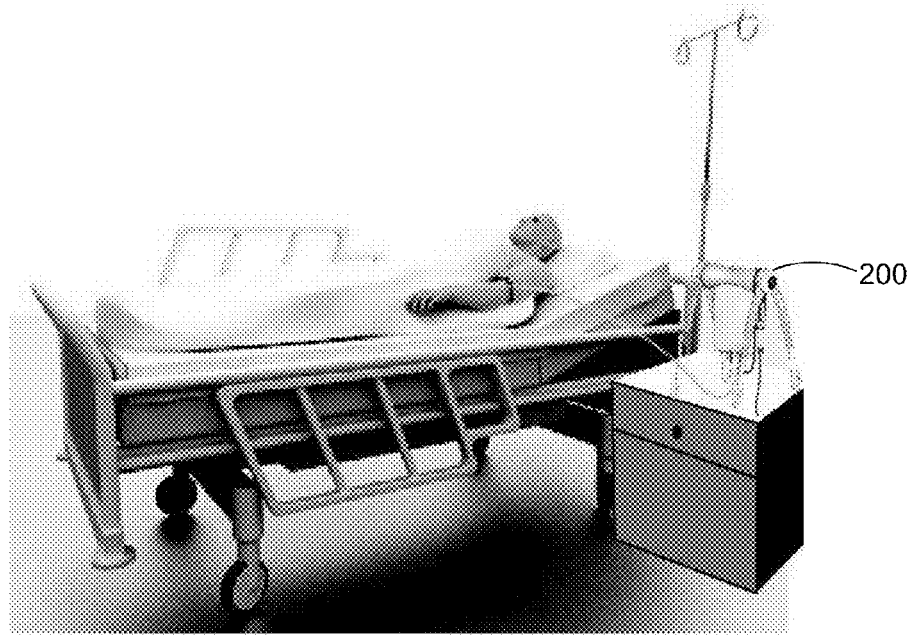
FIGS. 3A to 3G are examples of some real-life scenarios in which the mobile infusion devices of FIG. 1A and FIG. 2A can be used.
Figure 3B:
Figure 3C:
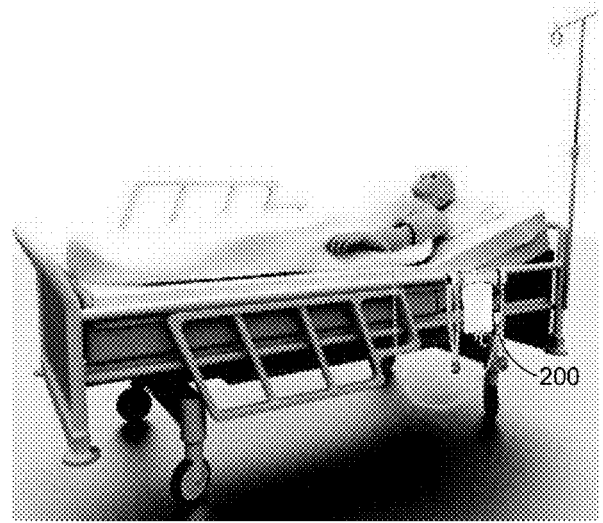

Referring now to FIGS. 3A to 3C, shown therein are various examples of some real-life scenarios in which the mobile infusion device 200 or the mobile infusion device 100 can be used in a flexible manner. FIG. 3A shows the mobile infusion device 200 with the pair of legs 204a and 204b in a mini-stand configuration and placed on a drawer, dresser, table or other surface beside a patient who is lying in a bed and requires infusion. FIG. 3B shows the mobile infusion device 200 with the pair of legs 204a and 204b in a mini-stand configuration and placed on the floor beside a patient who is lying in a bed and requires infusion. Alternatively, the mobile infusion device 100 can be hung from a conventional IV pole placed beside a patient who is lying in a bed and requires infusion and the mobile infusion device 100 can be easily removed off the IV pole when the patient needs to be mobilized and can carry the mobile infusion device by hand, on a shoulder with a strap and other ways. FIG. 3C shows the mobile infusion device 200 with the pair of legs 204a and 204b in a closed configuration and hung from a bed rail beside a patient who is lying in a bed and requires infusion.

Figure 3E:
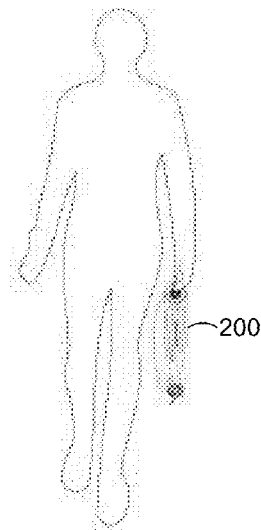
Figure 3D:
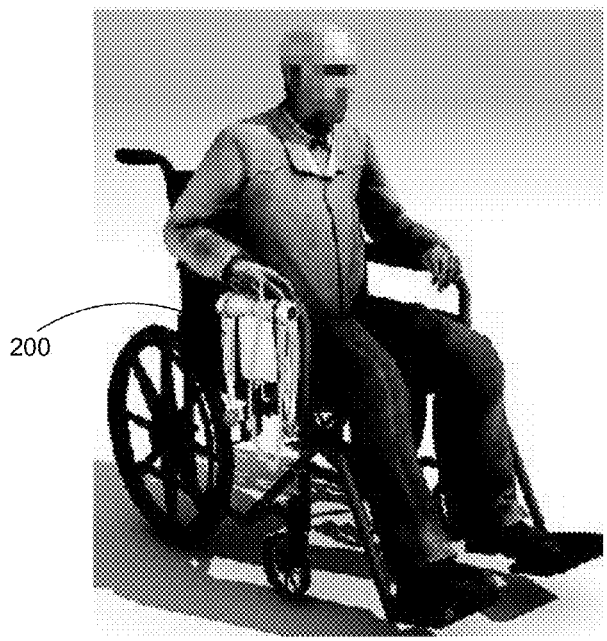
Figure 3F:
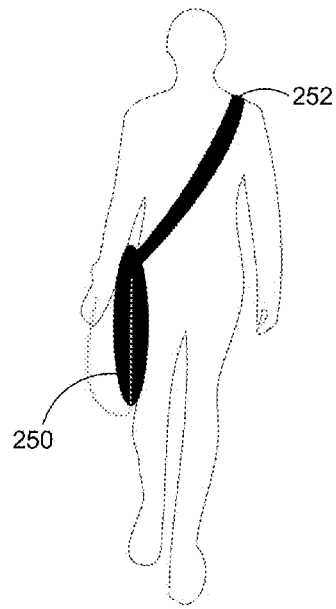
Figure 3G:
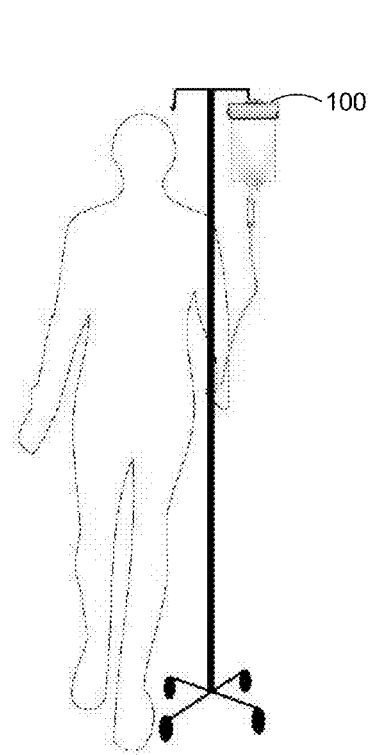

Referring now to FIGS. 3D to 3G, shown therein are various examples of some real-life scenarios in which the mobile infusion device 200 or the mobile infusion device 100 can be used in a flexible and portable manner. FIG. 3D shows the mobile infusion device 200 with the pair of legs 204a and 204b in a closed configuration and hung from an arm rest beside a patient who is seated in a wheel chair. Alternatively, in this case the mobile infusion device 200 can also be held by the patient or placed on the patient's laps. FIG. 3E shows the mobile infusion device 200 with the pair of legs 204a and 204b in a closed configuration and being held by a patient as the patient walks to a desired location. FIG. 3F shows a bag or pouch 250 that can be used to carry the mobile infusion device 200. It should be noted that the bag 250 can be any sort of suitable bag like a carry-on or a backpack, for example. The bag 250 has a shoulder strap 252 that is placed on the patient's shoulder to maintain the mobile infusion device 200 in a stable position as the patient walks to a desired location. In some embodiments, a mold may be included in the bag 250 which forms a snug fit with the mobile infusion device 100 or 200 thereby providing increased protection during use. FIG. 3G shows the mobile infusion device 100 hung from a conventional IV pole which is then moved by the patient as the patient walks to a desired location.

Figure 4A:
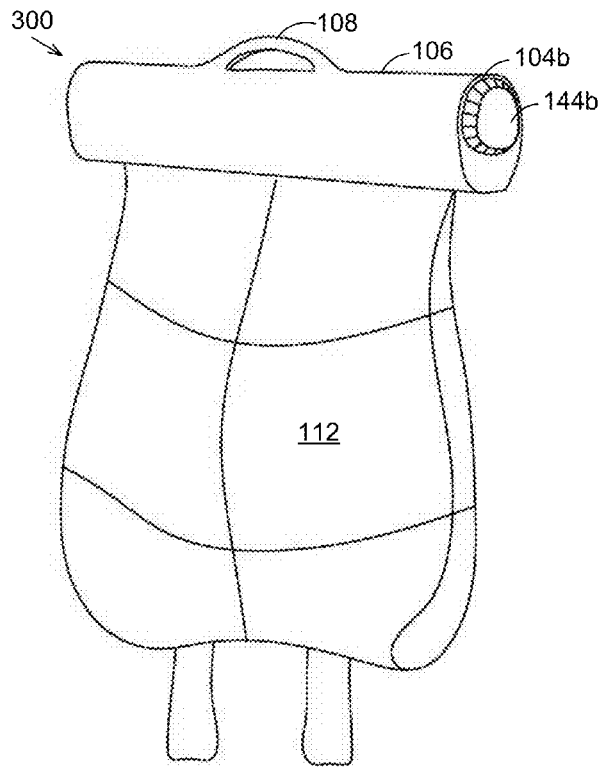
FIG. 4A is a front perspective view of another example embodiment of a mobile infusion device.
Figure 4B:
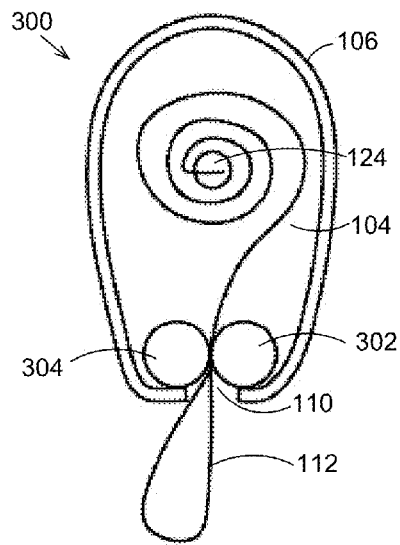
FIG. 4B is a cross-sectional view of the mobile infusion device of FIG. 4A in which an IV bag has been used and is nearly empty.

Referring now to FIGS. 4A and 4B, shown therein are front perspective and side cross-sectional views, respectively, of another example embodiment of a mobile infusion device 300. The mobile infusion device 300 is similar to the mobile infusion device 100 except that the pressure applicator comprises two members 302 and 304 that are disposed near the bottom opening 110 of the housing 106. The two members 302 and 304 have outer surfaces that are in close proximity to one another near the bottom opening 110 of the housing 106. The two members 302 and 304 extend along a substantial portion of the longitudinal axis of the chamber 104 and are long enough to apply pressure evenly to the IV bag 112 as it is drawn into the central chamber 104 by the rotation of the roller 124 during operation. The two members 302 and 304 can be two rods, two rollers, two squeegees, a single roller or a rod and a squeegee, a cable, a rectangular horizontal post or a wall, and the like.

Figure 4C:
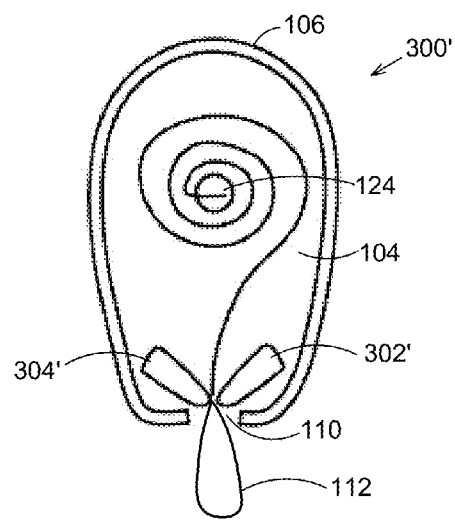
FIG. 4C is a cross-sectional view of an alternative embodiment of the mobile infusion device of FIG. 4A in which the IV bag has been used and is nearly empty.

Referring now to FIG. 4C, shown therein is a cross sectional view of an alternative embodiment of the mobile infusion device 300' in which the IV bag 112 has been mostly used. In this example embodiment, the mobile infusion device 300' is similar to the mobile infusion device 300 except that the two members 302' and 304' are wedge-shaped or conical-shaped bars that are disposed near the bottom opening 110 of the housing 106 and have two outer surfaces that are in close proximity to one another but have a gap between them through which the IV bag 112 passes as it is pulled up by the roller 124 during operation. Again, the two members 302' and 304' extend along a substantial portion of the longitudinal axis of the chamber 104 and are long enough to apply pressure evenly to the IV bag 112 as it is drawn into the central chamber 104 by the rotation of the roller 124 during operation.

Referring now to FIGS. 5A and 5B, shown therein is a front perspective view and a partial cross-sectional view of another example embodiment of a mobile infusion device 350. The mobile infusion device 350 comprises a slot or opening 352 at a top portion of the housing 106' for allowing a portion of the IV bag 112 to be expelled from the mobile infusion device 350 after the IV bag 112 has been pulled up into the mobile infusion device 350.

In this example embodiment, the roller 126 is replaced by two members 354 and 356 that extend along a substantial portion of the horizontal axis of the inner chamber of the mobile infusion device 350 and have a gap between them through which the IV bag 112 is pulled. One of the two members 354 and 356 can rotate while the other is stationary in order to pull up the IV bag 112. In alternative embodiments, both members 354 and 356 can rotate to pull up the IV bag 112. Both of the members 354 and 356 have a pliable outer surface that is coated with a flexible material, such as rubber, to provide an improved grip on the IV bag 112 as it is being pulled. The outer surface can have various forms such as, but not limited to, a flat surface, longitudinal capillary lines and so forth. In an alternative embodiment, only one of the members 354 and 356 has a pliable outer surface. In some embodiments, gear-like structures 354a and 356a can be used as shown to improve the grip of the rollers 354 and 356 on the IV bag 112.

Alternatively, any of the mobile infusion device embodiments described herein can be modified to include an upper chamber above the central chamber for storing the empty portion of the IV bag 112.

Referring now to FIG. 5C, shown therein is a cross-sectional view of an interior portion of an alternative embodiment of a mobile infusion device 350'. The mobile infusion device 350' is similar to the mobile infusion device 350 except that the two members 354' and 356' that form the pressure applicator have quasi-square housings 358a and 358b that each have shoulders or chamfered edges (or angled walls) 360a and 362a and 360b and 362b, respectively, with gaps between the shoulders. The gaps in the walls of the housings 358a and 358b face one another. The two members 354' and 356' further comprise rollers 364a and 364b, respectively. The two members 354' and 356' and their components extend along a substantial portion of the longitudinal axis of the inner chamber of the mobile infusion device 350' for a length that is at least slightly larger than the widest IV bag 112 which is intended for use with the mobile infusion device 350'. The rollers 364a and 364b have outer surfaces a portion of which is proximal to one another but have a gap therebetween through which the IV bag 112 is passed when the IV bag 112 is pulled into the mobile infusion device 350' during use. The rollers 364a and 364b rotate about their longitudinal axes to pull the IV bag 112 between them thereby exerting a substantially constant pressure on the IV bag 112 to expel the fluid out of the IV bag 112 during use. In an alternative embodiment, only one of the rollers 364a and 364b rotates while the other one is stationary. The chamfered edges 362a and 362b provide some pressure to the top portion of the IV bag 112 as well as guide the IV bag 112 towards the rollers 364a and 364b. The chamfered edges 360a and 360b guide the empty top portion of the IV bag 112 towards the upper part of the central chamber and prevent the empty top portion of the IV bag 112 from rolling around the roller 364a or the roller 364b.

The angled walls 362a and 362b are disposed on a first side of the rollers 364a and 364b defining an entry pathway for the IV bag 112 between the rollers 364a and 364b and the angled walls on 360a and 362b are on opposite side of the rollers 364a and 364b and define an exit pathway out of the rollers 364a and 364b for the IV bag 112.

Figure 6A:
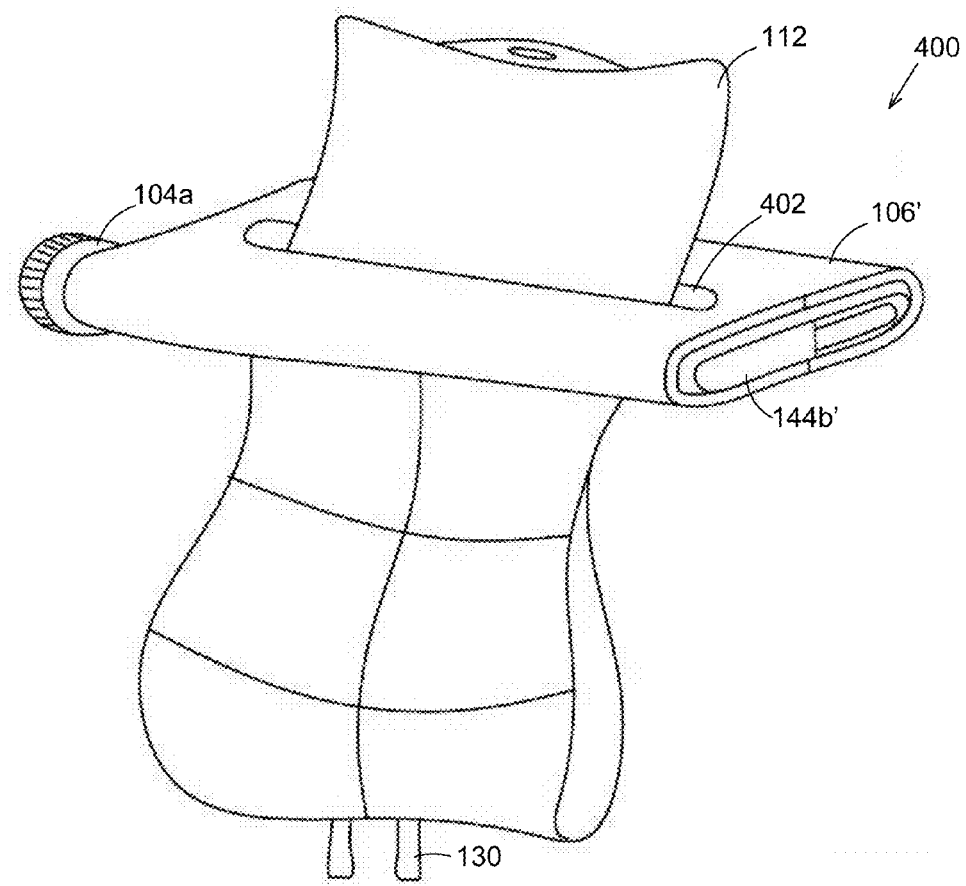
FIG. 6A is a front perspective view of another example embodiment of a mobile infusion device.

Referring now to FIG. 6A, shown therein is a front perspective view of another example embodiment of a mobile infusion device 400. The mobile infusion device 400 comprises a slot or opening 402 at a top portion of the housing 106' for allowing a portion of the IV bag 112 to be expelled from the mobile infusion device 400 after the IV bag 112 has been pulled up into the mobile infusion device 400. In this example embodiment, the control button 144b' is flatter with a different design, and can be activated either as push buttons or sliding switches, for example.

Figure 6B:
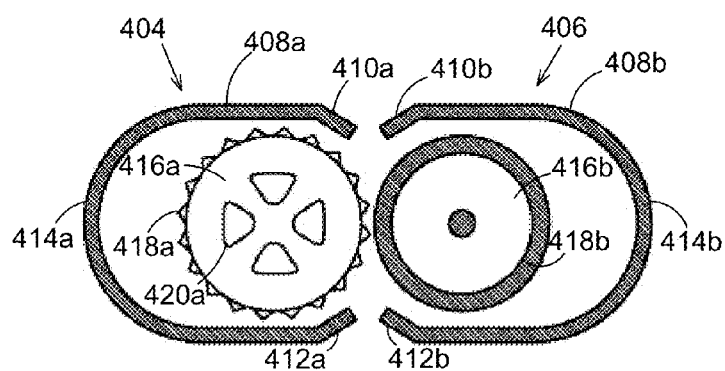
FIG. 6B is a cross-sectional view of a portion of the mobile infusion device of FIG. 6A.

Referring now to FIG. 6B, shown therein is a partial cross-sectional view of the mobile infusion device 400 in which the pressure applicator comprises two members 404 and 406. The two members 404 and 406 are somewhat similar to the two members 354' and 356'. The two members 404 and 406 comprise housings 408a and 408b that have shoulders or chamfered edges 410a and 412a and 410b and 412b, respectively, with gaps between the shoulders. The gaps in the housings 408a and 408b face one another. The housings 408a and 408b further comprise rounded sides 414a and 414b, respectively. The chamfered edges or angled walls 410a and 412a and 410b and 412b provide an added safety feature since the narrow gap between 410a and 410b as well as 412a and 421b reduces the chance that a foreign object can be inserted by accident or not into the mobile infusion device 200 (e.g. kids inserting their fingers, toys, etc.). The chamfered edges or angled walls 410a and 412a and 410b and 412b also provide extra layers of pressure applicators.

The two members 408a and 408b further comprise rollers 416a and 416b, respectively. The two members 408a and 408b and their components extend along the longitudinal axis of the inner chamber of the mobile infusion device 400 for a length that is substantially similar to or at least as long as the widest IV bag 112 which is intended for use with the mobile infusion device 400. In this context, substantially similar to means that the members 408a and 408b may have a length that is a bit shorter than the widest IV bag 112 which is intended for use with the mobile infusion device 400 while still allowing the members 408a and 408b to provide substantially constant pressure to the IV bag 112 during use to expel fluid from the IV bag 112 (this length and pressure feature of the members 408a and 408b applies to the various embodiments of the mobile infusion device described herein).

The rollers 416a and 416b have outer surfaces 418a and 418b with portions that are proximal to one another but have a gap through which the IV bag 112 is passed when the IV bag 112 is pulled into the mobile infusion device 400. During operation, the rollers 416a and 416b rotate about their longitudinal axis to pull the IV bag 112 between them thereby exerting a substantially constant pressure on the IV bag 112 to expel fluid out of the IV bag 112. In an alternative embodiment, only one of the rollers 416a and 416b rotates while the other one is stationary. In an alternative embodiment, only one of the rollers 416a and 416b is driven by a drive spring and the rollers 416a and 416g can be geared together.

In this example embodiment, the surface 418a of the roller 416a is a non-smooth surface (e.g. pointed edges) while the surface 418b of the roller 416b is smooth and somewhat pliable. The non-smooth surface 418a enhances the grip of the roller 416a on the IV bag 112. The slots 420a can be used for the main shaft/rod that connects to the spring mechanism through various bearings and bushings.

It should be noted that each of the mobile infusion devices 300, 300', 350, 350' and 400 can be modified to include two pairs of legs as in the case of the mobile infusion device 200, thereby further increasing the usability and portability of these devices.

Figure 7A:
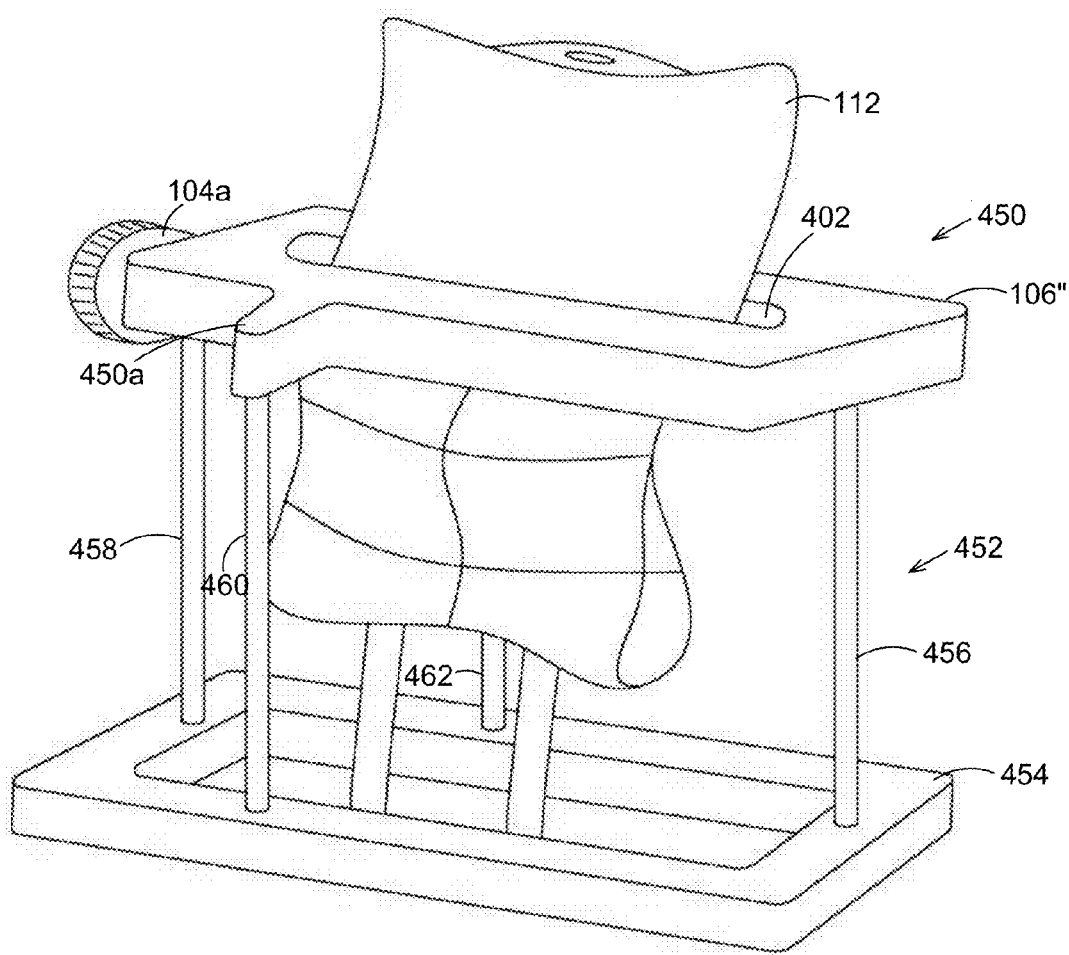
FIG. 7A is a front perspective view of another example embodiment of a mobile infusion device.

Referring now to FIG. 7A shown therein is a front perspective view of another example embodiment of a mobile infusion device 450. The mobile infusion device 450 is similar to the mobile infusion device 400 except that the mobile infusion device 450 comprises a stand 452 upon which the mobile infusion device 450 can be placed. In this example embodiment, the stand 452 comprises a base 454 and several vertical support members 456 to 462 that connect the base 454 to the mobile infusion device 450. The base 454 comprises a rectangular frame and the vertical support members 456 to 462 are rods or posts. An upper surface of the base 454 and a lower surface of the mobile infusion device 450 comprise apertures that are sized to releasably receive the vertical support members 456 to 462 via a friction fit. The vertical support members 456 to 462 have a sufficient length or height such that the bottom of the IV bag 112 does not touch the surface upon which the base 454 rests during use. Furthermore, the housing 106" of the mobile infusion device 450 comprises a protrusion 540a to which the vertical support member 460 is releasably attachable. This allows the base 454 to have a perimeter that is larger than the housing 106" of the mobile infusion device 450 which provides greater stability. In alternative embodiments, the vertical support members 456 to 462 can be in different locations as long as there is sufficient structural integrity for the stand 452.

In alternative embodiments, the base 454 and/or the vertical support members 456 to 462 can have different shapes and/or cross-sections. For example, there can be pairs of alternative support members located near the locations of the vertical support members 456 to 462 and these pairs of alternative support members do not have to be disposed in a vertical fashion as the support members 456 to 462 but rather each pair can be slanted to form a crisscross pattern or an X-shaped pattern.

Figure 7B:
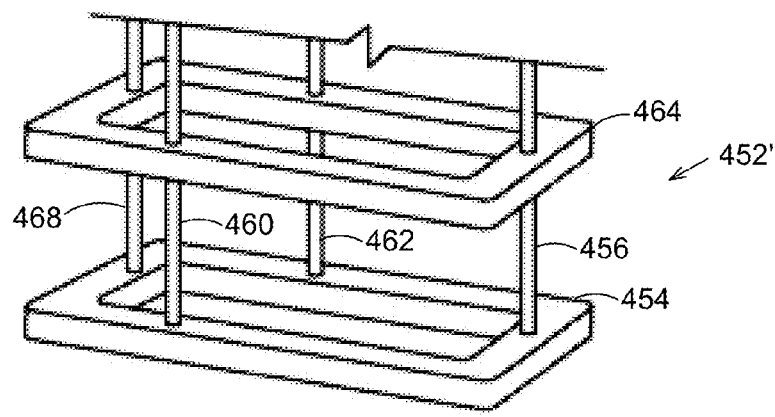
FIG. 7B is a partial front perspective view of another example embodiment of a stand that can be used with the mobile infusion device of FIG. 7A.

Referring now to FIG. 7B, shown therein is an example of an alternative embodiment of a stand 452' that can be used with the mobile infusion device 450. The base 452' comprises a horizontal support member 464 that has apertures through which the support members 456 to 462 pass. The horizontal support member 464 provides further structural stability for the stand 452'. The horizontal support member 464 can be placed at the mid-point of the support members 456 to 462 between the mobile infusion device 450 and the base 454. In alternative embodiments, there can be more than one horizontal support member.

In alternative embodiments, there can be apertures throughout the housing 106" where the vertical support members 456 to 462 can be actuation devices such as gears or rollers so that the housing 106" moves downwards while squeezing fluid out of the IV bag 112.

Figure 8:
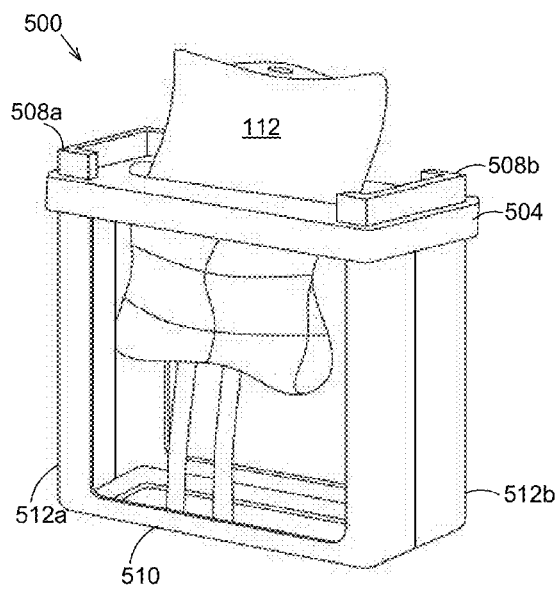
FIG. 8 is a front perspective view of another example embodiment of a mobile infusion device.

Referring now to FIG. 8, shown therein is a front perspective view of another example embodiment of a mobile infusion device 500. The mobile infusion device 500 is similar to the mobile infusion device 400 except that the mobile infusion device 500 comprises a stand 502 upon which the mobile infusion device 500 can be placed. The mobile infusion device 500 has a housing 504 with a center aperture or slot 506 through which the IV bag 112 is passed as it is pulled up into the mobile infusion device 500. The housing 504 also comprises a pair of apertures (not shown) disposed near either end of the mobile infusion device 500 that are configured to releasably engage posts 508a and 508b on the upper portion of the stand 502. The posts 508a and 508b include a lip, flange or shoulder on at least a portion of their outer surface upon which the bottom surface of the mobile infusion device 500 sits. The stand 502 also comprises a base 510 and two side walls 512a and 512b that are connected to the base 510. The posts 508a and 508b are formed at the top portion of the side walls 512a and 512b respectively. The sidewalls 512a and 512b are spaced apart to form a frame with large openings through which the IV bag 112 can be moved when the IV bag 112 is being loaded or unloaded from the mobile infusion device 500. The sidewalls 512a and 512b have a sufficient height such that the bottom of the IV bag 112 does not reach below the base 510 during operation. The base 510 may also comprise an aperture to reduce the weight of the stand 502.

For the example embodiments shown in FIGS. 7A to 8, the stands 452 and 502 can be static, in which case, during use, the IV bag 112 is drawn into the bottom opening where pressure is applied to expel fluid out of the IV bag 112 and the empty portion of the IV bag 112 is then expelled out of the top opening of the mobile infusion devices 450 and 500. Alternatively, the stands 452 and 502 can be dynamic, in which case, during use, the IV bag 112 is held in position while the mobile infusion devices 450 and 500 move downward applying pressure to the IV bag 112 to expel fluid out of the IV bag 112 and the empty portion of the IV bag 112 is then expelled out of the top opening of the mobile infusion devices 450 and 500. This can be accomplished by using gear tracks as is described with respect to FIGS. 9A to 9C.

Figure 9A:
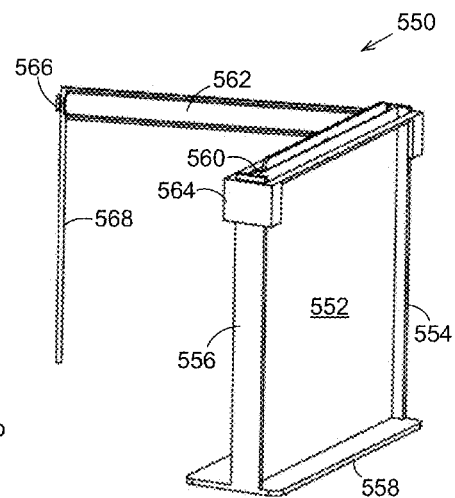
FIGS. 9A to 9B are front and rear perspective views, respectively, of another example embodiment of a mobile infusion device in an open position.
Figure 9B:
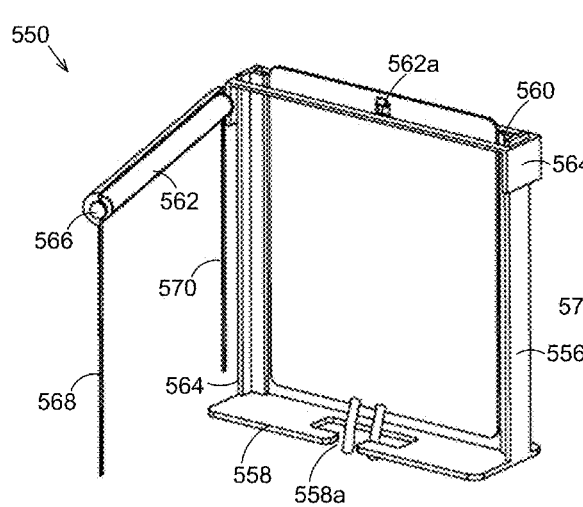
Figure 9C:
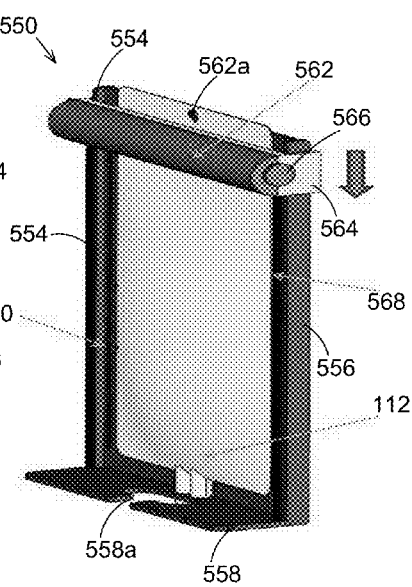
FIG. 9C is a front perspective view of the mobile infusion device of FIG. 9A in a closed position.

Referring now to FIGS. 9A to 9B, shown therein are front and rear perspective views, respectively, of another example embodiment of a mobile infusion device 550 in an open position and FIG. 9C is a front perspective view of the mobile infusion device 550 in a closed position. The mobile infusion device 550 comprises a back plate 552, a pair of sidewalls 554 and 556, a base 558 with an aperture 558a, an upper frame 564 that defines an upper slot 560 and has a hook 562a, as well as a roller 562 with two gear tracks 568 and 570. The back plate 552 is used to hold the IV bag 112 in place during use. A portion of the upper frame 564 is pivotally coupled to a portion of the gear track 570 which allows the roller 562 along with the gear tracks 568 and 570 to pivot away from the back plate 552 into an open position thereby allowing for the insertion or removal of the IV bag 112. Once a new IV bag 112 is inserted along the back plate 552 and engages the hook 562a, the roller 562 and the gear tracks 568 and 570 can be pivoted to a closed position in which these elements rest along the back plate 552 and/or the upper frame 564. The roller 562 also comprises a gear wheel at each end thereof. The roller 562 has a length such that the gear wheels engage with the gear tracks 568 and 570 when the roller is pivoted to the back plate 552. A spring is also attached to each end of the roller 562 and these springs are used to force the roller 562 along the back plate 552, thereby applying pressure to expel the fluid in the IV bag 112 as the roller 562 moves downward. The springs are located on the side walls 554 and 556. They are connected to the ends of the roller 562 and when the IV bag 112 is in place, the roller 562 is held firmly on the front surface of the IV bag 112 from the top and that triggers and activates the springs which are pre-wound (they can be manually pressed downwards). To stop the operation of the roller a latch on the frame 566 is actuated. Closing the latch on the frame 566 again closes the "circuit" and retriggers the springs that continue from where they left off.

Figure 10A:
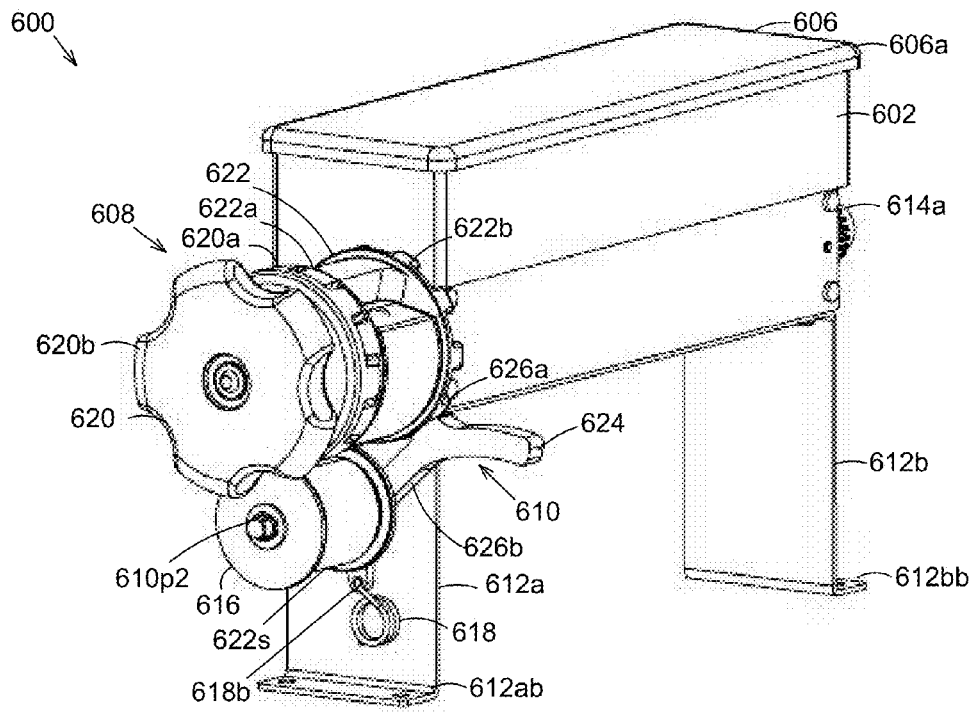
FIG. 10A is a front-left perspective view of another example embodiment of a mobile infusion device.
Figure 10B:
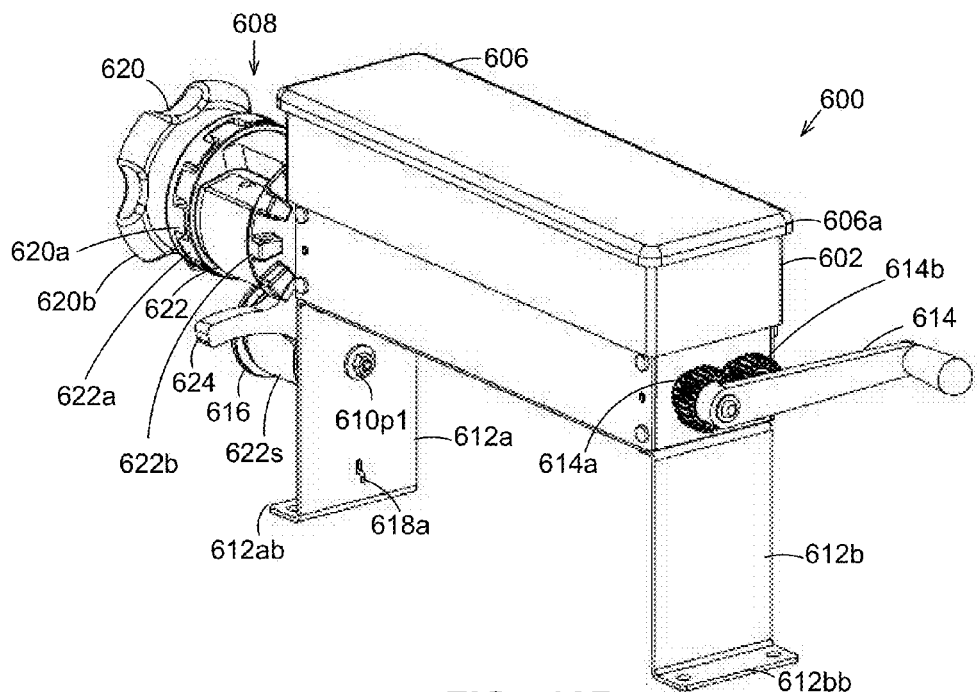
FIG. 10B is a front-right perspective view of the mobile infusion device of FIG. 10A.
Figure 10C:
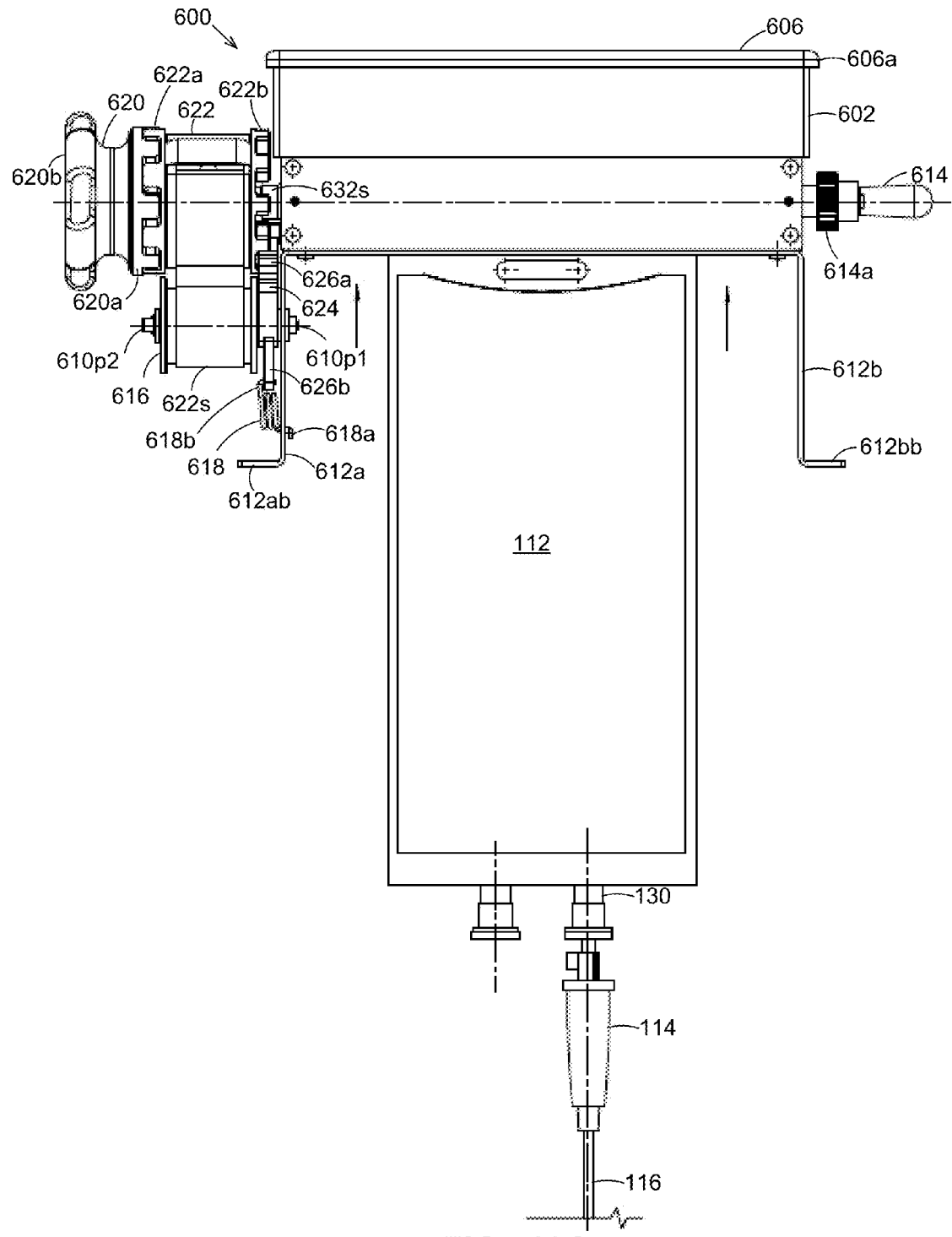
FIG. 10C is a front view of the mobile infusion device of FIG. 10A in which an IV bag is being loaded for use.
Figure 10G:
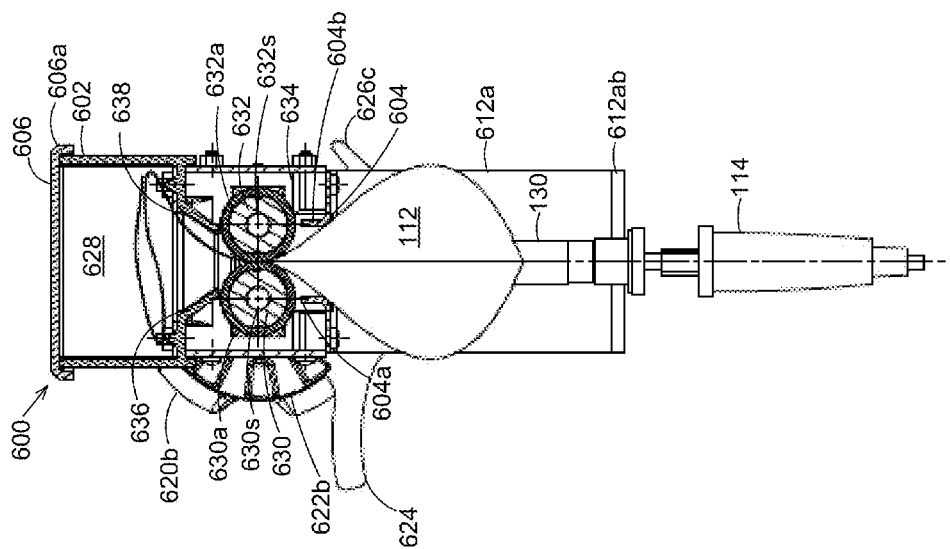
FIG. 10G is a cross-sectional side view of the mobile infusion device of FIG. 10A along the line B-B of FIG. 10F.
Figure 10F:
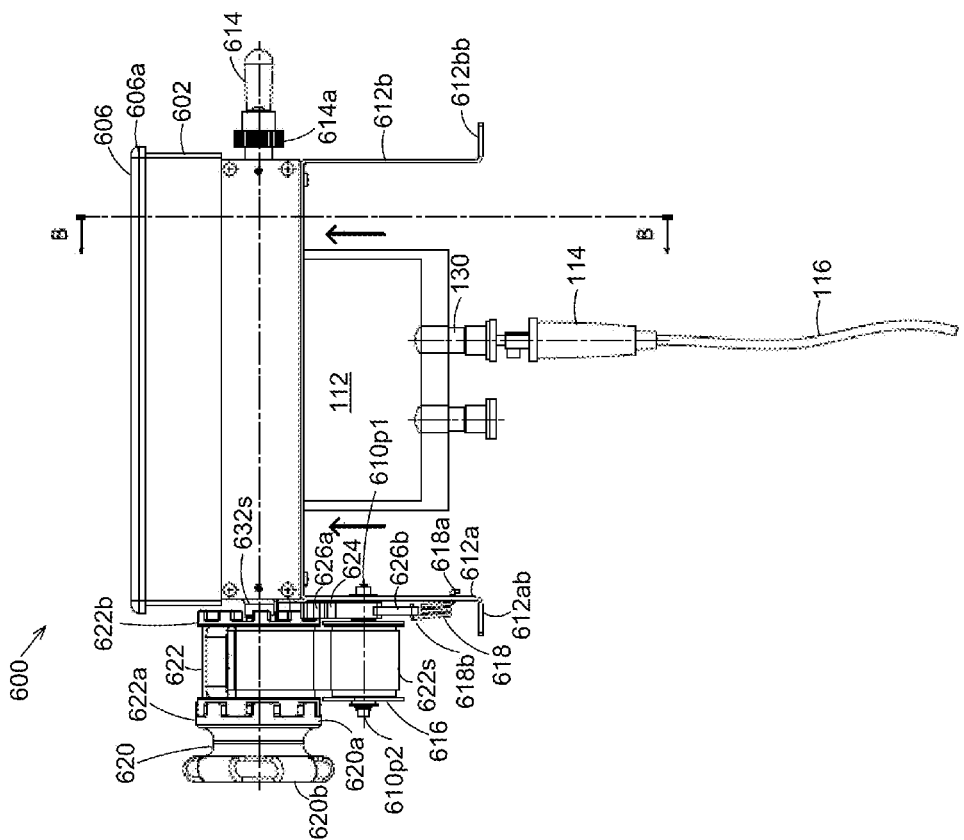
FIG. 10F is a front view of the mobile infusion device of FIG. 10A in which an IV bag has approximately 30% of the fluid left.
Figures 10H, 10I:
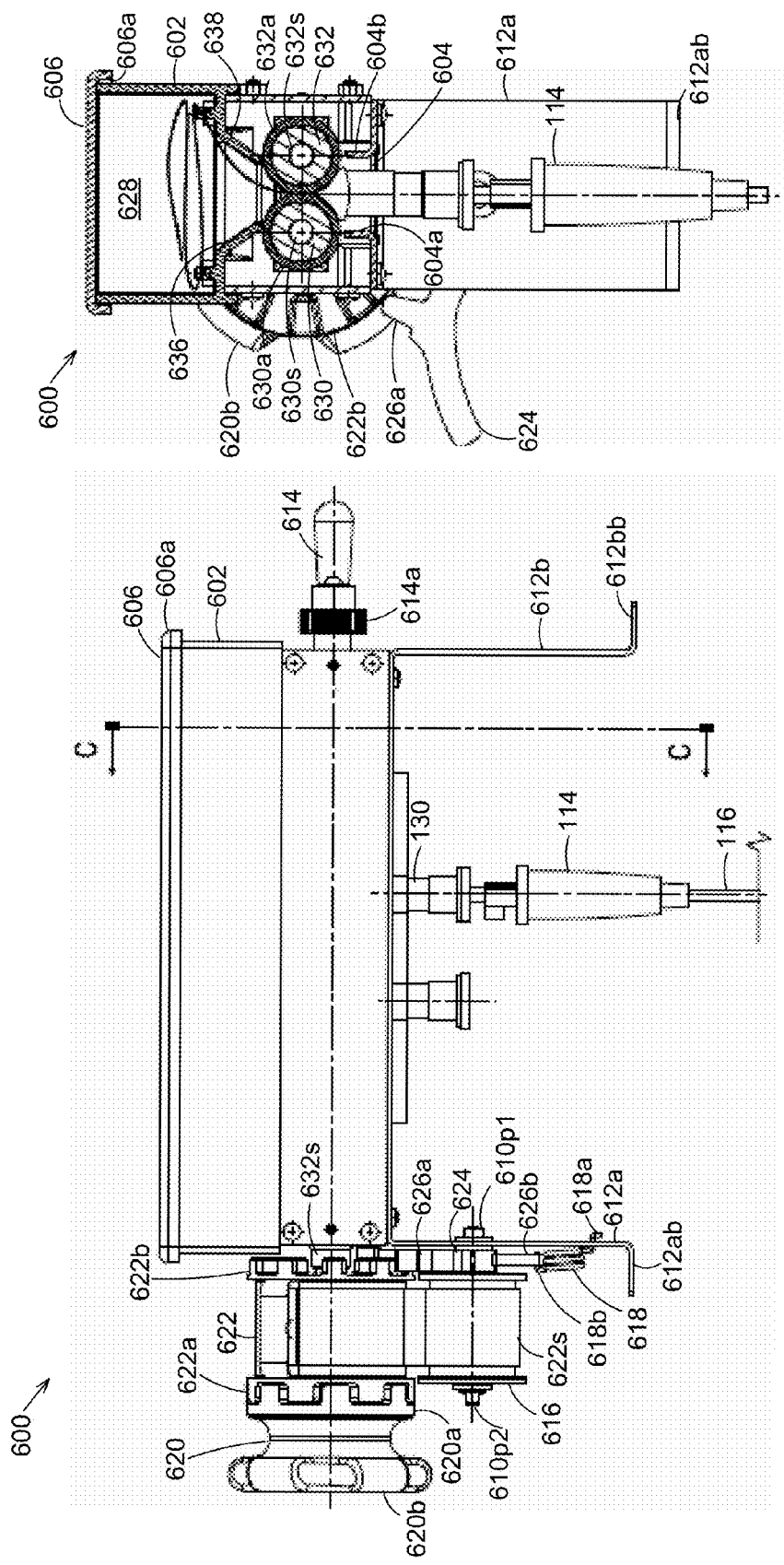
FIG. 10H is a front view of the mobile infusion device of FIG. 10A in which an IV bag has been entirely used.
FIG. 10I is a cross-sectional side view of the mobile infusion device of FIG. 10A along the line C-C of FIG. 10H.
Figure 10J:
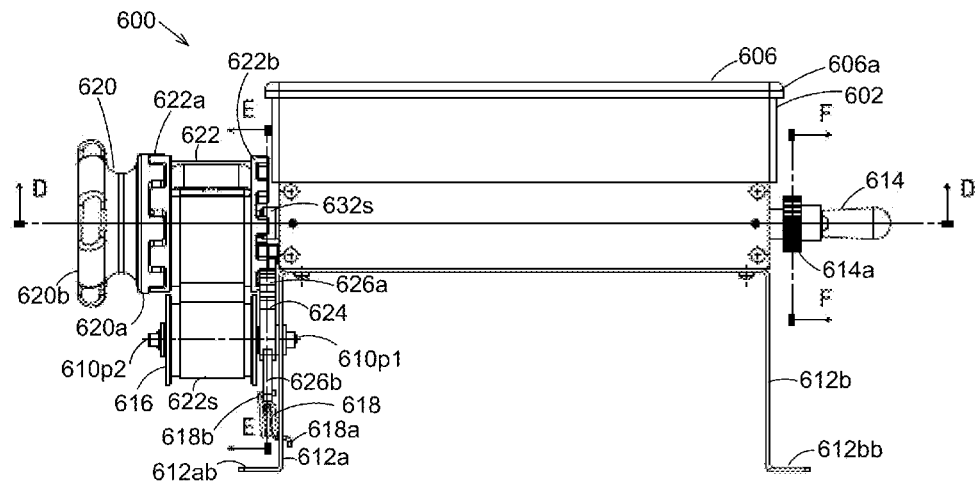
FIG. 10J is a front view of the mobile infusion device of FIG. 10A with no IV bag.
Figure 10K:
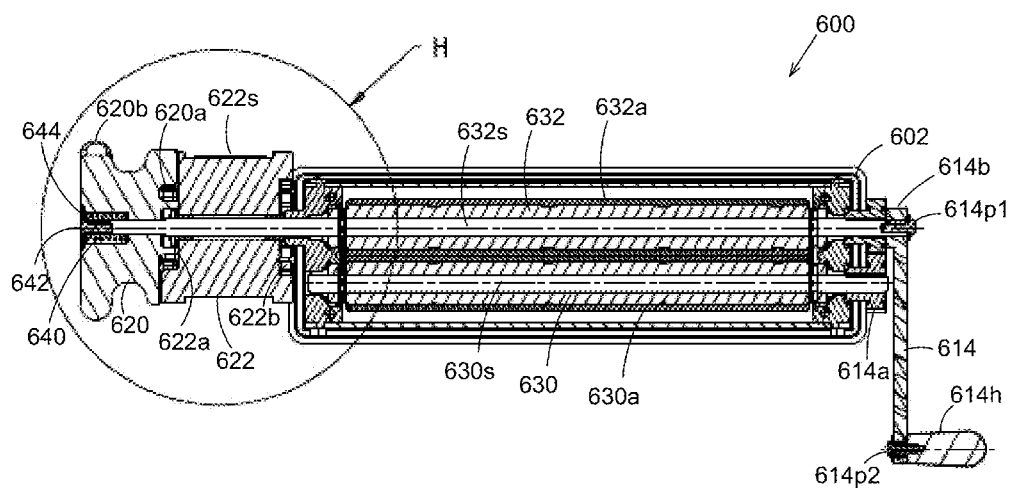
FIG. 10K is a cross-sectional bottom view of the mobile infusion device of FIG. 10A along the line D-D of FIG. 10J.
Figure 10P:
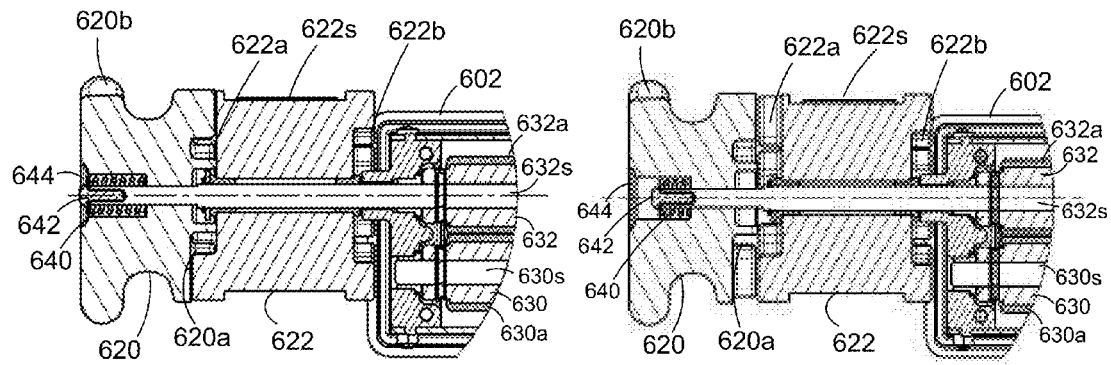
FIG. 10P is a cross sectional side view of the mobile infusion device of FIG. 10A along the line F-F of FIG. 10J.
Figure 10P:
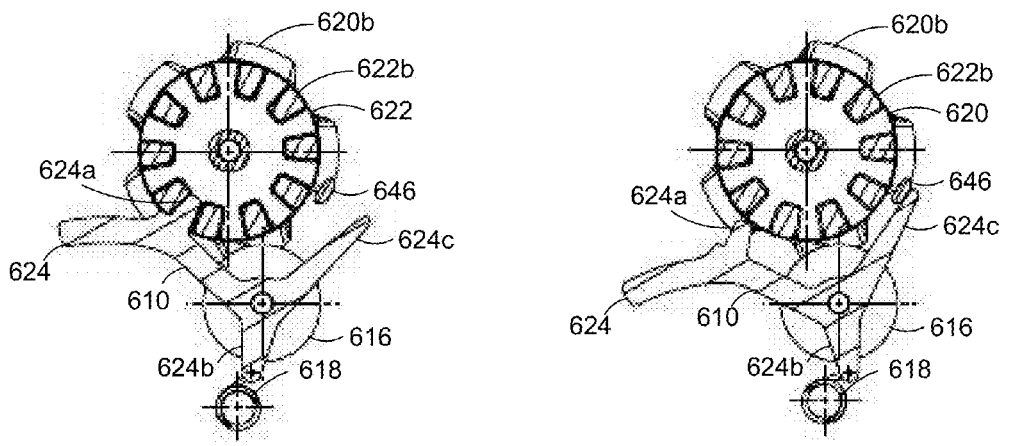

FIGS. 10A to 10P show various views of another example embodiment of a mobile infusion device 600. The mobile infusion device 600 has various operational and structural similarities with the other various mobile infusion devices described herein such as having start, stop and standby modes of operation and using spring-based action to apply a substantially constant force to expel fluid from an IV bag during use.

Referring now to FIGS. 10A and 10B, shown therein are front-left and front-right perspective views, respectively, of the mobile infusion device 600. The mobile infusion device 600 comprises a housing 602, a bottom opening 604 defined by a first portion of the housing 602, a cover 606, a latch mechanism 608, a lever 610, legs 612a and 612b, a crank 614, a spool 616, a drive spring 622a and a spring 618. The latch mechanism 608 comprises a knob 620 and a drive member 622. The lever 610 comprises a handle 624 as well as first, second and third engagement members 626a, 626b and 626c.

With reference to FIG. 10E, the mobile infusion device 600 further comprises an upper chamber or hopper 628 defined by a second portion of the housing and two rollers 630 and 632 disposed along a longitudinal axis of the mobile infusion device 600 within a central chamber 634. The upper chamber 628 comprises first and second angled walls 636 and 638 that are adjacent to but spaced away from the rollers 630 and 632. The walls 636 and 638 guide the used or empty portion of the IV bag 112 into the hopper 628. In this example embodiment, the rollers 630 and 632 are geared to each other and have exterior surfaces 630a and 632b that are made of soft rubber to improve their grip on the IV bag 112 during use (alternatively the entirety of the rollers 630 and 632 can be made from this material). The outer surfaces 630a and 632a of the rollers 630 and 632, respectively, may contact with one another or may be slightly spaced apart such that they can contact opposite sides of the IV bag 112 during use. The outer surfaces 630a and 632a can be an overmolded material that helps improve the grip of the rollers 630 and 632 on the IV bag 112 during use. The rollers 630 and 632 are mounted on shafts 630s and 632s, respectively.

The crank 614 is coupled to the rollers 630 and 632 in order to turn the rollers 630 and 632 to expel the IV bag 112 and recharge or reload the rotation assembly for subsequent use. Referring now to FIG. 10K, in this example embodiment, the crank 614 is directly coupled to the roller 632 by receiving one end of a shaft 632s of the roller 632 in an aperture at one end of the crank 614 and a fastener 614p1 is used to secure the crank 614 to the roller 632. The crank 614 is also coupled to the roller 630 via gears 614a and 614b. Gear 614a has an aperture that is sized to receive the shaft 632s of the roller 632 in a friction fit that allows the gear 614a to rotate when the roller 632 rotates or the crank 614 is rotated. The gear 614b is similarly coupled to one end of a shaft 630s of the roller 630 via a friction fit. The gear 614b also meshes with the gear 614a so that when the gear 614a rotates the gear 614b also rotates which causes the roller 630 to rotate. This helps to prevent the roller 630 from slipping when the roller 632 rotates. Accordingly, the gears 614a and 614b act as twin gears to synchronize the rollers 632 and 630. Each of the gears 614a and 614b has a smaller rounded portion with a smooth exterior that are proximal to the housing 602 and are received by apertures or bearings within the housing 602 such that the gears 614a and 614b are coupled to the housing 602 but are also able to rotate during use. The crank 614 also comprises a handle 614h which is coupled to the main body of the crank 614 via a fastener 614p2. The fasteners 614a and 614b can be any suitable fasteners such as pins or screws, for example.

Referring once again to FIGS. 10A and 10B, the housing 602 provides a protective shell for the inner components of the mobile infusion device 600 and is made of any suitable sturdy, lightweight material such as different types of plastic, aluminum or other materials, for example. There can be alternative embodiments in which the housing 602 has a different shape or can have smoother and more rounded edges.

The bottom opening 604 is located at the bottom wall of the housing 602 and provides access to the interior of the mobile infusion device 600 so that the IV bag 112 can be loaded and ejected during use. Off the shelf IV bags, administration kits and tubing that are commonly used today in the marketplace can be used with the mobile infusion device 600 (as well as with the various other embodiments described herein). Therefore, the bottom opening 604 has a length that is larger than the widest IV bag 112 which is intended to be used with the mobile infusion device 600 and the bottom opening is preferably large enough to accommodate all conventional IV bag sizes. Alternatively, there may be different sizes of the mobile infusion device 600 to accommodate different size IV bags and different applications as was described for the mobile infusion device 200. Furthermore, the length of the bottom opening 604 is selected to provide some extra clearance in the event that the IV bag 112 may not be inserted straight into the rollers 630 and 632 but rather may be out of alignment which will cause it to move upward on a bit of an angle; the extra length of the opening 604 accommodates such scenarios. The bottom opening 604 is also defined by upper sidewalls 604a and 604b which guide the IV bag 112 towards and between the rollers 630 and 632 or away from the rollers 630 and 632 depending on the operation of the mobile infusion device 600 (i.e. whether the IV bag 112 is being loaded and used or is being removed).

In this example embodiment, the cover 606 is removable and has an outer shoulder or flange 606a which is sized to removably engage the housing 602 in a friction-fit. This allows the cover 606 to be removed when the mobile infusion device 600 requires servicing or trouble-shooting. In alternative embodiments, the cover 606 may be connected to the housing 602 using one or more hinges or other tabs which engage protrusions or depressions on the outer surface of the housing 602. In alternative embodiments, the cover 606 is not removable but forms a continuous part of the housing 602. In this case, the upper chamber 628 is formed by an inner surface of the housing 602 which is one integral piece.

It should be noted that in at least one alternative embodiment, the mobile infusion device 600 has a handle disposed near a top portion of the housing 602 to allow a patient, medical practitioner, caregiver or other individual to carry or hold the mobile infusion device 600 during use.

The legs 612a and 612b are used to keep the bottom of the housing 602 a certain distance above a resting surface upon which the bases 612ab and 612bb of the legs 612a and 612b rest so that the bottom of the IV bag 112 is not below the resting surface. In this example embodiment, the bases 612ab and 612bb are flanges but they can have different forms or shapes in different embodiments. It should be noted that in alternative embodiments, the legs 612a and 612b can be replaced by the legs shown in FIGS. 2A-2I, FIG. 7A or FIG. 8. It should be noted that the legs 612a and 612b are optional in some embodiments which are used in applications that do not require the mobile infusion device 600 to have legs such as when the mobile infusion device 600 is hung from an object like an IV pole, a rail on a bed, or a rail on a wheelchair.

Furthermore, when the legs 612a and 612b are not used, then the mobile infusion device 600 can be placed in a carry-on bag. In some implementations, the carry-on bag can have a molded surface that is complimentary to various portions of the housing 602 to protect the mobile infusion device 600 when it is carried in the carry-on bag.

It should be noted that there can also be alternative embodiments in which a drip chamber holder is suspended from a portion of the housing 602 of the mobile infusion device 600 in a similar manner as the drip chamber holder 618 for the mobile infusion devices 100 and 200. The drip chamber holder in any of these embodiments may be made from silicon, plastic, rubber or other suitable material. In addition, in these embodiments, the IV connector 130c may also be used.

There can be cases when a spherical drip chamber is used without a drip chamber holder simply because a spherical drip chamber does strictly not need to be in an upright position. In fact, using the spherical drip chamber further enhances the ability of the patient to use the mobile infusion device in any environment, any position and height. The spherical drip chamber will always maintain the infusion fluid vertically and its spherical shape prevents any air bubbles from entering the IV tubing and thus endangering the patient.

The latch mechanism 608 is used to engage and disengage the roller 632 and an actuator that is used to rotate the roller 632 during use. The shaft 632s of the roller 632 acts as a drive shaft. In this example embodiment, the actuator is a drive spring 622a which is shown and described in more detail with respect to FIGS. 10K to 10M. In this example embodiment, the drive spring 622a is a constant force spring that is wound during production. In alternative embodiments, other actuators may be used such as, but not limited to, other types of springs, such as a clock spring and the like.

The knob 620, the drive member 622, the spring 640, the roller 632, the gears 614a and 614b and the roller 630 are the main components of the rotation assembly for the mobile infusion device 600 that is used to pull the IV bag 112 upwards and expel fluid from the IV bag 112 or push the IV bag 112 downwards to remove the IV bag 112 from the mobile infusion device 600. The components of the rotation assembly are selected to provide a suitable amount of force or pressure to the IV bag 112 to expel fluid therefrom or to otherwise move the IV bag 112 for a variety of bag types and sizes. However, the components can be selected differently in different embodiments to provide a greater or lesser amount of force as is needed by the particular application of the mobile infusion device 600. These components and the operations of the mobile infusion device 600 will be described in more detail.

The knob 620 and the drive member 622 of the latch mechanism 608 have surfaces that can releasably engage one another. The drive member 622, which can also be referred to as a drum, has a first engagement surface 622a with ridges or teeth that is disposed towards the knob 620. The knob 620, which can also be referred to as a clutch or a latch, has a first engagement surface 620a with ridges or teeth that is disposed towards the engagement surface 622a of the drive member 622 and a surface 620b with ridges to allow a patient, medical practitioner or caregiver to grip and manipulate the knob 620. During use, when the knob 620 is engaged with the drive member 622, the ridges on the engagement surfaces 620a and 622a interlace with one another. In this case, the drive spring 622a, drive member 622 and the knob 620 are engaged along with the extended shaft 632s of the roller 632 which allows the roller 632 to rotate depending on the position of a control mechanism (described in more detail below). The knob 620 can also be pulled out and away from the drive member 622 so that the roller 632 is not loaded and can be more easily turned by the crank 614. The knob 620 can be disengaged from the drive member 622 when the control mechanism is in a stop position (i.e. stop mode).

The drive member 622 is also coupled to the extended shaft 632s of the roller 632 (this can be seen more clearly in FIG. 10K). The drive member 622 has an inner channel extending therethrough which is shaped to receive and form a tight fit with the outer surface of the extended shaft 632s of the roller 632 (bearings or other elements may be used to achieve the tight fit). Therefore, in use, the drive member 622 rotates when the roller 632 rotates. The drive member 622 also has a second engagement surface 622b that is disposed towards the housing 602. The second engagement surface 622b has ridges or teeth that interact with the control mechanism.

The control mechanism comprises the spring 618 and the lever 610. Together these elements work with the drive spring 622s, the drive member 622 and the knob 620 of the latch mechanism to allow the mobile infusion device 600 to be used in a particular mode or state. In this example embodiment, there are three modes: standby mode, start mode and stop mode. In these modes, the lever 610 and the knob 620 have particular positions to enable certain functionality as will now be described.

The handle 624 of the lever 610 is an example of a user interface that allows a user to set the mode of operation for the mobile infusion device 600 since the user can lower and raise the handle 624 to perform certain operations. The lever 610 has a first position (shown in FIG. 10N) in which the engagement member 626a engages one or more ridges on the engagement surface 622b of the drive member 622 which prevents the drive member 622 and the roller 632 from rotating. When the lever 610 is in this position, the mobile infusion device 600 can be in standby mode or in stop mode depending on whether the knob 620 (i.e. the clutch or latch) is engaged or not. The lever 610 has a second position (shown in FIG. 10O) in which the handle 624 is pulled down so that the engagement member 626a no longer engages the ridges on the engagement surface 622b and this allows the drive member 622 and the roller 632 to rotate depending on the position of the knob 622, as will be described below. In the second position, the third engagement member 626c of the lever 610 rests against a post 646 so that the lever 610 does not interfere with the motion of the drive member 622. The post 646 is part of the housing 602.

The lever 610 is pivotally coupled to the housing 602 and the spool 616. In this example embodiment, a fastener assembly with ends 610p1 and 610p2 extends from the housing 602 through the lever 610 and the spool 616 and allows the lever 610 to be movable between the first (locked) position and the second (unlocked) position. In this example embodiment, the fastener assembly includes a bolt along with a nut and several washers. In alternative embodiments, other elements can be used for the fastener assembly. The second engagement member 622b is also coupled to the housing 602 via the spring 618.

The spool 616 is coupled to the side of the lever 610 that is distal to the housing 602. The spool 616 is also coupled to the drive member 622 via the drive spring 622a. The spool 616 rotates as the roller 630 rotates because the drive spring 622s is being wound onto the spool 616. The spring 618 provides a force to maintain the lever 610 in the current position that is selected by the user. The spring 618 can be referred to as a toggle torsion spring.

A first end 618a of the spring 618 is coupled to the housing 602 and a second end 618b of the spring 618 is coupled to the engagement member 626b of the lever 610. The spring 618 is a torsion spring that can be used as a toggle in order to maintain the lever 610 in either the first or second position after the lever 610 has been moved by a patient, medical practitioner, caregiver or other individual.

It should also be noted that the drive member 622 is coupled to the spool 616 by the drive spring 622s. A first portion of the drive spring 622s is coiled around the spool 616 and a second portion of the drive spring 622s is coiled around a portion of the drive member 622. The first and second portions of the drive spring 622s vary during the operation of the mobile infusion device 600. For example, when the drive spring 622s is recharged or reloaded, there is a greater amount of the second portion of the drive spring 622s wrapped around a greater portion of the drive member 622 than when the mobile device is operated in start mode or is in stop mode after being used. When the mobile infusion device 600 is operated in start mode, the drive member 622 is free to rotate and the drive spring 622s will have a natural tendency to wrap around the spool 616. As more of the drive spring 622s wraps around the spool 616, the drive member 622 is rotated in a counter-clockwise manner which causes the shaft 632s and the roller 632 to rotate in a counter-clockwise manner. This motion is transferred to the roller 630 by the gear mechanism made up of gears 614a and 614b such that the roller 630 rotates in an opposite direction to the rotation of the roller 632s. The rotation of the rollers 630 and 632 cause the IV bag 112 to be pulled upwards and a force to be exerted on the IV bag between the rollers 630 and 632 to expel the fluid from the IV bag 112. It should be noted that the drive member 622 is much larger than the spool 616 which provides a mechanical advantage to drive the rollers 632 and 630. For example, the sizes of the drive member 622 and the spool 616 can be selected so that there is approximately a 2:1 advantage to drive the system. Other sizes for these components can be selected in other embodiments.

In the standby mode, the spring 622s is recharged or reloaded and is ready for initial use with the IV bag 112. In order to enter into the standby mode, the lever 610 is in the unlocked position and the knob 620 is pulled out. The knob 620 or the crank 614 can then be turned in the opposite direction that the roller 632 turns during start mode to recharge the drive spring 622s. Once the drive spring 622s has been recharged, the lever 610 is moved up to the locked or stop position and the knob 620 is engaged with the drive member 622. The drive spring 622s mounted on the drive member 622, and the spring 640 are engaged together with the shaft 632s of the roller 632. At this point the IV bag 112 can be loaded into the mobile infusion device 600 by feeding the top portion of the IV bag 112 into the bottom opening 604 to make contact with the bottom edges of the rollers 630 and 632. The handle 624 of the lever 610 can then be pulled down which will disengage engagement member 626a of the lever 610 from the engagement surface 622b, which will allow the drive member 622 and the roller 632 to turn in a counter-clockwise fashion while the roller 630 rotates in a clockwise fashion. This will result in a pulling force at the top portion of the IV bag 112 thereby pulling the IV bag 112 upwards and when the IV bag 112 has been pulled up a sufficient amount (e.g. such that liquid is just about to be but is not yet expelled from the IV bag 112), the lever 610 can then be pulled up to the locked position so that the engagement member 628a engages the engagement surface 622b of the drive member 622 to prevent the drive member 622 and the rollers 632 and 630 from rotating. At this point the control mechanism is in a standby position (in other words standby mode).

During standby mode, when a patient, medical practitioner, caregiver or another individual wishes to use the mobile infusion device 600, the handle 624 of the lever 610 is pulled downwards to the unlocked position so that the engagement member 624a disengages from the engagement surface 622b of the drive member 622. This allows the drive member 622 and the rollers 630 and 632 to start rotating such that the IV bag 112 is pulled upwards. Accordingly, the rollers 630 and 632 now act as pull up and pinch rollers providing a substantially uniform pressure or force to the IV bag 112 to expel the fluid out of the IV bag 112 to the drip chamber 114. This is the start mode. During start mode the knob 620 is engaged with the drive member 622 and the drive spring 622s is engaged with the shaft 632s of the roller 632 thereby driving the roller 632.

During start mode, when the patient, medical practitioner, caregiver or another individual wishes to stop the operation of the mobile infusion device 600, the handle 624 of the lever 610 is pulled upwards to the locked position so that the engagement member 624a engages the engagement surface 622b of the drive member 622 thereby preventing the drive member 622 and the rollers 630 and 632 from rotating such that the IV bag 112 is now stationary and no force is being applied to the fluid within the IV bag 112. This is stop mode. The knob 620 is still engaged with the drive member 622.

During stop mode, if the patient, medical practitioner, caregiver or another individual wishes to restart the operation of the mobile infusion device 600, the handle 624 of the lever 610 is pulled downward to the unlocked position so that the engagement member 624a again disengages from the engagement surface 622b of the drive member 622. This allows the drive member 622 and the rollers 630 and 632 to continue rotating such that the mobile infusion device 600 carries on from where it was stopped and the IV bag 112 is pulled upwards once again. The rollers 630 and 632 now continue to provide a pulling and pinching force to apply a substantially uniform pressure or force to the IV bag 112 to expel the fluid within the IV bag 112 to the drip chamber 114. This is the continuation of the start mode. The knob 620 is still engaged with the drive member 622.

When it is desired to remove the IV bag 112 regardless of whether it is empty, standby mode is used. To enter standby mode, the handle 624 of the lever 610 is first pulled upwards to the locked position to place the mobile infusion device 600 into stop mode as described above. The knob 620 of the latch mechanism is then pulled out and turned (depending on the implementation the knob 620 may be turned a quarter of a full turn) so that the engagement surfaces 620a and 622a no longer engage one another. At this point, the knob 620 can be slightly turned so that the knob 620 can be released by the user and the engagement surfaces 620a and 622a now no longer engage one another as the ridges on these surfaces now contact one another. The crank 614 is then turned so that the roller 632 now turns clockwise and the roller 630 turns counter-clockwise. This then moves the top portion of the IV bag 112 that is in contact with the rollers 632 and 630 downwards. The crank 614 is turned the required number of turns until the topmost portion of the IV bag 112 is clear of the rollers 630 and 632. At this point the IV bag 112 simply comes lose. It should be noted that during this process, the spring 622s is recharged or reloaded since it has been turned by the turning of the roller 632 (due to the crank 614) in the opposite direction that it turns when the mobile infusion device 600 is in start mode. The number of crank turns that it takes to eject the IV bag 112 is exactly the number of turns or the length that the drive spring 622s traveled to move the IV bag 112 to the position it was in before the crank 614 was turned. Accordingly, during standby mode the drive spring 622s is recharged and ready for use with a new IV bag 112.

Alternatively, during standby mode, in order to remove the IV bag 112 and recharge the drive spring 622s, the IV bag 112 can be grabbed at the bottom and manually pulled out down. This will turn the rollers 632 in the opposite direction that it turns during the start mode thereby recharging the drive spring 622s. However, it may require less effort to use the crank 614 to recharge the drive spring 622s due to the additional torque provided by the crank handle 614h.

Regardless of which technique is used to recharge the drive spring 622s, the lever 610 is moved to the lock position to maintain tension on the drive spring 622s that has just been reloaded.

In alternative embodiments, there can be different sizes that are used for various components such as the lever 610 along with the handle 624 and the engagement members 626a to 626c. There can also be different sizes for the drive spring 622s, the crank 614, the knob 620, the drive member 622 and the various elements on the engagement surfaces thereof.

Referring now to FIG. 10C, shown therein is a front view of the mobile infusion device 600 in which the IV bag 112 is being loaded for use. The IV bag 112 is first introduced to the rollers 630 and 632 and the mobile infusion device 600 is in standby mode and the knob 620 is engaged with the drive member 622. To load the IV bag 112, the handle 624 can be pulled down momentarily as explained previously so that the rollers 630 and 632 rotate to pull up the IV bag 112. When a sufficient amount of the top portion of the IV bag 112 has been pulled up such that there is no force exerted to expel the fluid in the IV bag 112, the lever 610 can be pulled back up to stop the rotation of the rollers 630 and 632. Also shown in FIG. 10C is the end of the bottom of the IV bag 112 where standard tubing is located including the nozzle 130 and the drip vial or drip chamber 114 (which is used to monitor flow rate). A flow-rate adjustment valve is located further down the tubing 116 and is not shown. In some cases, the flow-rate adjustment valve and the corresponding thumb roller controller can be positioned near the mobile infusion device 600 by using something similar to the drip chamber holder 118 so that the thumb roller controller will not be accessible and susceptible to accidental movement. Alternatively, or in addition thereto, the thumb roller valve can be covered by a protective cover that snaps and locks around the thumb roller valve once the flow rate has been set. The cover can have a childproof opening so that it can only be opened by an adult who would then set the thumb roller valve to achieve the desired flow rate. It should be noted that there can be embodiments which use both a spherical drip chamber and the protective cover for the thumb roller valve.

Referring now to FIG. 10D, shown therein is a front view of the mobile infusion device 600 in which the IV bag 112 has been partially used. At this time, the IV bag 112 has approximately 70% of its fluid left. FIG. 10E is a cross-sectional side view of the mobile infusion device 600 along the line A-A of FIG. 10D. The IV bag 112 is pulled up and pinched between the rollers 630 and 632 which are applying a substantially constant pressure or force to expel fluid from the IV bag 112. The empty portion of the IV bag 112 is starting to enter the upper chamber 628 of the housing 602.

Referring now to FIG. 10F, shown therein is a front view of the mobile infusion device 600 in which the IV bag 112 has approximately 30% of the fluid left. FIG. 10G is a cross-sectional side view of the mobile infusion device 600 along the line B-B of FIG. 10F. The IV bag 112 is pulled up and pinched between the rollers 630 and 632 which are still applying a substantially constant pressure or force to expel fluid from the IV bag 112. This is approximately the same amount of force that was used when the IV bag 112 had more fluid in it. A larger empty portion of the IV bag 112 is now in the upper chamber 628 of the housing 602 after being guided thereto by the angled walls 636 and 638. The angled walls 636 and 638 also prevent the empty portion of the IV bag 112 from rolling around one of the rollers 630 and 632 during start mode.

Referring now to FIG. 10H, shown therein is a front view of the mobile infusion device 600 in which the IV bag 112 has been entirely used and there is no more fluid left. FIG. 10I is a cross-sectional side view of the mobile infusion device 600 along the line C-C of FIG. 10H. The IV bag 112 is prevented from being completely pulled into the mobile device 600 due to the nozzle 130 and other hard plastic IV fittings that contact with and stop at the bottom of the rollers 130 and 132. This is the end of the usage of the IV bag 112. If IV therapy is to continue and another IV bag 112 is to be used, the shaft 632s of the roller 632 can be rotated to recharge the drive spring 622s and remove the IV bag 112 by using the crank 614 as explained previously. At the end of this recharging process, the knob 620 is then re-engaged to the drive member 622 and the lever 610 is moved to the locked position thereby placing the mobile infusion device 600 in standby mode.

Referring now to FIG. 10J, shown therein is a front view of the mobile infusion device 600 with no IV bag 112 loaded. The knob 620 of the latch mechanism is engaged with the drive member 622 and the drive spring 622s is fully charged. Various sectional and expanded views are shown in FIGS. 10K to 10P to further illustrate the various components of the mobile infusion device 600 in order to show how they operate with one another during use.

Referring now to FIG. 10K, shown therein is a cross-sectional bottom view of the mobile infusion device 600 along the line D-D of FIG. 10J. The knob 620 is shown in the engaged position with the drive member 622 and the drive spring 622s is engaged with the shaft 632s of the roller 632. This allows the drive spring 622s to drive the roller 632 when the lever 610 is moved down to the second position (i.e. unlocked position) so that the mobile infusion device 600 operates in start mode.

When an IV bag 112 is to be loaded in the mobile infusion device 600, the knob 620 can be pulled out, and then a first hand can be used to place the upper portion of the IV bag 112 between the bottom surfaces of the rollers 630 and 632 and a second hand can be used so that the roller 632s can be turned just enough to grip and pull up a portion of the IV bag 112. In an alternative embodiment, the second hand can hold the mobile infusion device 600 by the handle (not shown) and also actuate a nearby located standby button which will enable half a turn of the roller 632 which is just enough to grip and pull up a top portion of the IV bag 112. In either of these embodiments, the knob 620 can then be released to re-engage the drive member 622 and the lever 610 can be pulled up into the locked position. The same process can be used in reverse to remove the IV bag 112 from the mobile infusion device 600. In an alternative embodiment, the knob 620 is designed such that when it is pulled out and disengaged from the drive member 622, the knob 620 can remain in that position without necessarily requiring the user to hold onto the knob 620.

Referring now to FIGS. 10L and 10M, shown therein are magnified views of the portion H of the mobile infusion device 600 shown in FIG. 10K. FIGS. 10L and 10M show the latch mechanism in engaged and disengaged positions, respectively. The position and operation of the various elements of the rotational assembly shown in FIG. 10L was previously described in relation to FIG. 10K.

When the latch mechanism is disengaged, as is shown in FIG. 10M, the knob 620 has been pulled away from the drive member 622 such that the engagement surfaces 620a and 622a no longer engage one another. This place a compressive force on the spring 640 since it is coupled to the end of the shaft 632s of the roller 630 by a fastener 642. The fastener can be a screw, a pin or the like. This distal end of the spring 640 then moves away from the surface 644 of the knob 620. The drive spring 622s can then be recharged or reloaded when the crank 614 is turned in the opposite direction of the rotational direction of the roller 632 during start mode. When the drive spring 622s has been sufficiently recharged, the knob 620 is moved towards the drive member 622 so that the engagement surfaces 620a and 622b engage one another and the drive spring 622s can drive the rotational movement of the roller 632 during start mode. In addition, the lever 610 is moved to the locked position to maintain tension on the drive spring 622s. It should be noted that the spring 640 is used to move the knob 620 towards the drive member 622 when the knob is released by a user's hand.

Referring now to FIGS. 10N and 10O, shown therein are cross-sectional side views of the mobile infusion device 600 along the line E-E of FIG. 10J. FIGS. 10N and 10O show the latch 610 in engaged and disengaged positions, respectively. When the lever 610 is in the engaged position (shown in FIG. 10N), the engagement member 624a of the lever 610 engages ridges or teeth on the engagement surface 622b of the drive member 622 thereby preventing rotation of the rollers 632 and 630. The lever 610 can be in this locked position during either stop mode or standby mode. When the lever 610 is in the disengaged or unlocked position (shown in FIG. 10O), the engagement member 624a of the lever 610 disengages and is clear of the ridges or teeth on the engagement surface 622b of the drive member 622 which allows the rollers 632 and 630 to rotate. The lever 610 is in this unlocked position during start mode.

Referring now to FIG. 10P, shown therein is a cross sectional side view of the mobile infusion device 600 along the line F-F of FIG. 10J. FIG. 10P shows the crank 614 and the gears 614a and 614b in more detail. The crank 614 is connected to the gear 614a so that rotation of the crank 614 drives the gear 614a. The teeth of the gear 614a engage the teeth of the gear 614b so that rotation of the crank 614 also drives rotation of the gear 614b which in turn drives rotation of the shaft 630s of the roller 630. Since the gears 614a and 614b are the same size the gear ratio is 1:1 and so the rollers 632 and 630 will rotate at the same speed during use.

In at least one alternative embodiment, a constant force clock type spring can be used for the drive spring 622s so that the spool 616 is not needed. Furthermore, the clock spring and the drive member 622 can be located inside the housing 602 while the knob 620 and the crank 614 are outside of the housing 602. This will make the device smaller in size, more lightweight and easier to use. Weight and size are very important especially for patients like children and older people as the weight of the mobile infusion device adds to the weight of the IV bag so a light-weight mobile infusion device will be easier to carry and move around. Also since IV therapy lasts for long hours the ease of mobilizing a lighter and smaller mobile infusion device by such patients is an important factor in adopting and getting used to the product and technology.

In at least one alternative embodiment, that may include the constant force clock type spring, the control mechanism is located closer to a handle that would be disposed near a top portion of the housing 602. This allows a user of the mobile infusion device to use one hand to operate the control mechanism and to disengage and re-engage the knob 620 while using the other hand to hold onto the IV bag 112 in order to load or remove the IV bag 112. Alternatively, there can be embodiments in which the control mechanism is in other suitable locations.

In at least one alternative embodiment, that may include the constant force clock type spring and in which the control mechanism can be located at a top portion, a side portion or another area of the housing 602, the control mechanism comprises different elements for actuation by a user. For example, the control mechanism can be spring-loaded buttons, slide switches or toggle switches which have a first surface that is on the outside of the housing 602 and forms part of the user interface that the user can manipulate between first and second positions and a second control portion that is within the housing and has an engagement member disposed towards the engagement surface 622b of the drive member 622 to unlock or lock (i.e. allow or disallow) the rotation of the drive member 622 when the control mechanism is in the first and second positions, respectively.

In at least one alternative embodiment, that may include the constant force clock type spring, the location of the control mechanism at a top portion, a side portion or another area of the housing 602, and the control mechanism can have different actuators, there can be a mini-clutch or mini-latch mechanism for the crank 614 so that the crank 614 does not turn when the roller 632 is rotating. A mini-clutch can be implemented in the form of a push or pull button where the crank connects to the main gear 614a and the shaft 632s of the drive roller (i.e. roller 632). When this button is activated, the crank handle 614h disengages from the pivotal centre and thus the crank handle 614h will not rotate along with the gears 614a and 614b during operation in start mode. When the crank handle 614h and the crank 614 need to be used to eject the IV bag, the mini-clutch can be reversed to its original position where it re-engages the crank handle 614g back to the pivot centre of the crank 614. This is useful as there are less moving parts on the outside of the moving infusion device 600 during start mode, which is beneficial since a moving crank handle can be a safety issue since it can get caught up in the patient's clothing or another object.

Another alternative for the various embodiments described herein where the mobile infusion device has a crank, is that the crank can be attached to the clutch knob 620. This is advantageous since when the knob 620 is pulled out and disengaged from the drive member 622, the crank will still be connected to the main drive shaft 632s and is able to eject the IV bag 112 as described previously. This results in a nicer design and improved usability (i.e. ergonomics) for the mobile infusion device.

Another alternative for the various embodiments described herein where the mobile infusion device has a crank is that the crank can be foldable. Therefore, the crank can be folded towards the housing 602 when it is not used to reduce the chance of the crank getting caught on an object during start mode.

Another alternative for the various embodiments described herein where the mobile infusion device has a crank is that a ratchet can be used at the pivot location of the crank. When a user has stopped using the crank to recharge the drive spring, the ratchet prevents the crank from rotating so that the user can then move the lever 610 to the locked position so that tension in the drive spring will not be released.

Another alternative for the mobile infusion device 600 is that the crank 614 can be removed and the knob or manual action can then be used to remove the IV bag 112 and recharge the drive spring 622s.

Another alternative for the various embodiments of the mobile infusion devices described herein is the addition of a slow start suspension mechanism that is coupled to the spring mechanism to allow a smoother operation at the beginning of the start mode so that the user will not feel the full power of the drive spring all at once when it first starts to rotate the roller 632. The slow start suspension mechanism can be spring-based; for example a torsion spring may be used. Alternatively, the slow start suspension mechanism can be implemented by an air suspension. Alternatively, other mechanisms can be used to implement the slow start suspension mechanism.

Another alternative for the various embodiments of the mobile infusion device described herein is that user interface for the control mechanism includes a standby button, a start button and a stop button that are connected to components within the housing 602 to engage and disengage the drive member 620 as was described previously for the various modes. In this alternative example embodiment, the standby button is pressed first in order to load the IV bag 112. Pressing the standby button will turn the rollers 630 and 632 a quarter or a half turn, which is just enough to grip the top portion of the IV bag 112. If the start button is pressed before pressing the standby button, whether accidentally or not, then the rotation assembly will not rotate. Therefore, pressing the standby button is a precondition for pressing the start button and this precondition is a safety measure. The start button is pressed after the standby button which allows the rollers 630 and 632 to rotate and apply pressure to the fluid in the IV bag 112. The stop button can be pressed at any time to stop the rotation of the rollers 630 and 632. When it is time to unload the IV bag 112, the stop button is pressed and the lever 610 is left in the unlocked position, the knob 620 is disengaged and the crank 614 is turned the required number of times so that the IV bag 112 moves out of the mobile infusion device and is clear of the rollers 630 and 632 (alternatively the IV bag 112 can be pulled out by a user with a downward pulling motion). The slow start suspension mechanism may also be included.

It should be noted that for the various embodiments of the mobile infusion device described herein, various components can be designed such that the functionality is the same but the device is better suited for a particular application. For example, the various embodiments of the mobile infusion device described herein can be designed for specific use in veterinary or military applications. For these different applications, different sizes may be used for various components such as the frame that defines the bottom opening through which the IV bag 112 passes. Furthermore, the elements of the rotational assembly can be selected to provide greater or lesser amounts of force/pressure to the IV bag 112 during use.

The various embodiments of the mobile infusion device described herein can be made using a variety of materials depending on the requirements of the mobile infusion device for certain applications. In general, material such as polypropylene, recyclable plastic, aluminum and the like can be used. The various embodiments of the mobile infusion device described herein can be designed for use with multiple bags or a single bag, again depending on the particular application. This extends a patient's treatment options where there is a need to simultaneously infuse more than one IV bag to the patient.

It should be understood that all of the various embodiments of the mobile infusion device described herein can be used in at least one of the use scenarios shown in FIGS. 3A to 3G. It should also be noted that for all of the various embodiments of the mobile infusion device described herein, the patient, medical practitioner, or caregiver can adjust the flow rate by using a standard thumb roller valve which is part of IV administration kits commonly sold on the market.

It should be noted that the various embodiments of the mobile infusion device described herein can be modified to send an alert to the user whenever the tubing line is occluded or blocked due to bending of the tubing line. The alarm can be a sound and/or a visual alert that is triggered whenever there is an obstruction in the tubing line. This obstruction can be sensed by a flow sensor indicator that senses the flow of the fluid in the tubing and can be positioned anywhere along the tubing below the drip chamber towards the IV entry site to the patient. The sensor may be equipped with a display to provide flow rate and other pertinent data as well. The flow sensor can be implemented by using many different types of sensors such as, but not limited to, mechanical, pneumatic, electronic sensors and the like that are small enough to be easily mounted onto the tubing line. The alarm also receives information about the mode that the mobile infusion device is currently operating under. For example, information from the flow sensor can be considered only when the mobile device is operating in the start mode.

It should be noted that the various embodiments of the mobile infusion device described herein have features that provide a number of benefits. For example, with the various mobile infusion devices described herein, there is no need for gravity to expel the fluid so it can be used anytime, anywhere in almost any position. This feature results in increased mobility and freedom and a quality of life enhancement for users of the mobile infusion device (the users generally cover patients and animals, for example). This feature results in faster recovery time so less beds are occupied which reduces costs.

The various mobile infusion devices described herein are also small and light-weight thereby making it easier for a user to carry the device and be mobile. This also results in faster recovery time, since the users are more mobile, so beds are occupied for a smaller amount of time which reduces costs for healthcare providers.

At least some of the various mobile infusion devices described herein provide a one-click operation which makes the devices easier to handle and use, and the operation of the devices can be described in a simple and concise operator manual. Due to this ease of use, there is little or no need for a skilled operator to set up or provide special training, which reduces cost and frees up valuable resources for healthcare providers.

The various mobile infusion devices described herein can also be used with a variety of different bag sizes, which extends treatment options for users and allows infusion for a longer amount of time. Furthermore, one mobile infusion device can be used for a variety of IV infusion treatments, which also reduces costs for healthcare providers.

The various mobile infusion devices described herein do not require a power source or batteries and is therefore environmentally friendly. This allows users to use the device for extended hours of treatment, which saves time and money. This also significantly reduces overhead for healthcare providers by eliminating the need to recharge or replace batteries.

The various mobile infusion devices described herein can be made on a very cost-effective basis. Accordingly, more patients can afford to use the device. The affordable price also allows a healthcare provider to service more patients with greater effectiveness.

The various mobile infusion devices described herein also minimize disease spread which reduces the risk of contamination for users and allows for better control of disease spread by healthcare providers. The reduced risk is due to the fact that the mobile infusion devices described herein have a compact size and smaller weight and can be regarded and used as a personal infusion device that will be always with the patient and therefore be less susceptible to contamination and infectious spread of disease. Also, due to its compact size, cleaning and disinfecting the mobile infusion device is much easier, quicker and more cost-effective as cleaning requires fewer resources.

It should be noted that the term control assembly is meant to cover components that are used to allow the rollers to rotate during use. Accordingly, the control assembly can vary for different embodiments but an example of the control assembly is the lever 610, the spool 616 and the spring 618. Other examples of a control assembly include the working end of the control buttons 144a and 144b that engage or disengage the control of the drive spring.

It should also be noted that the term user interface for the control mechanism is meant to cover the portions of the control buttons that can be actuated by a user to control some function of the mobile infusion device, such as, but not limited to, the control buttons 144b and 212b that control rotation of the roller and connection of the legs, respectively, for the mobile infusion device 200, for example.

It should also be noted that the use of the term spring mechanism is meant to cover the drive spring(s) and associated structures that are used to impart rotational motion to at least one roller in the central chamber. Various examples of spring mechanisms are provided herein such as, but not limited to, the springs 208a and 208b, and the drive spring 622s along with the spool 616, for example.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

The invention claimed is:

1. A mobile infusion device that does not use gravity to expel fluid from a bag, wherein the mobile infusion device comprises:
   a housing including a first portion shaped to define a central chamber in the housing and a second portion shaped to define a first opening in the housing that is in communication with the central chamber and adapted to receive a portion of the bag during use;
   a rotation assembly mounted at a fixed location in the housing, the rotation assembly including a first member and a second member mounted in opposition to one another located within the central chamber and a spring mechanism operatively coupled to the first member to rotate the first member in order to move the bag between the first and second members thereby applying a force to a portion of the bag to expel fluid from the bag during use; and
   a control mechanism operatively coupled to the rotation assembly, the control mechanism having a control assembly to control rotation of the rotation assembly and a user interface coupled to the control assembly to allow a user to select one of a start mode, and a stop mode for the mobile infusion device during use,
   wherein the opening, the central chamber and the first and second members have a length that is long enough to accommodate bags of various sizes.

2. The device of claim 1, wherein the housing has a third portion shaped to define an upper chamber disposed above the central chamber, the upper chamber being shaped to receive an empty portion of the bag during use.

3. The device of claim 1, wherein a fourth portion housing is a cover that is removable to allow access to the central chamber.

4. The device of claim 1, wherein the housing has a fifth portion shaped to define a second opening in communication with the central chamber, the second opening being shaped to receive an emptied portion of the bag after it passes through the central chamber and allow the emptied portion of the bag to exit the device during use.

5. The device of claim 1, wherein the device comprises a handle located at an upper portion thereof to allow the device to be carried or moved during use.

6. The device of claim 5, wherein the user interface of the control mechanism is located near the handle to allow the user to hold and control the device using one hand.

7. The device of claim 1, wherein the bag is an Intravenous (IV) bag and the device further comprises a removable drip chamber holder having a first portion that is removably coupled to the housing and a second portion that is configured to releasably hold a drip chamber in a substantially vertical position.

8. The device of claim 7, wherein the device further comprises an IV connector having an angled portion that has a first end that is coupled to an exit nozzle of the IV bag and a second end that is coupled to regular IV tubing for infusion to a patient.

9. The device of claim 1, wherein the second drive member comprises a pressure applicator disposed within the central chamber and the first member comprises a single roller in close proximity to the pressure applicator, the single roller and the pressure applicator being configured to apply pressure to the bag as the bag passes therebetween during use.

10. The device of claim 9, wherein the pressure applicator is one of a rod, a squeegee, a roller, or a constriction member having slot with a width that is slightly larger than the thickness of the bag.

11. The device of claim 1, wherein the first member comprises an attachment member to releasably attach to the bag during use.

12. The device of claim 1, wherein the first member comprises one of a soft pliable outer surface and a non-smooth rough surface to improve grip on the bag during use.

13. The device of claim 1, wherein the housing comprises first and second endcaps disposed near opposite ends of the central chamber, the spring mechanism comprises a drive spring disposed within one of the endcaps and operatively coupled to a first end of the first member to transmit a drive force thereto during use, and the user interface comprises a control button coupled to the drive spring and disposed near the endcap having the drive spring, the control button being configured to allow a user to start and stop rotation of the first member.

14. The device of claim 1, wherein the housing comprises first and second endcaps disposed near opposite ends of the central chamber, the spring mechanism comprises a first drive spring disposed within the first endcap and a second drive spring disposed within the second endcap, the first and second drive springs being operatively coupled to opposite ends of the first member to transmit a drive force thereto during use, and the user interface comprises at least one control button coupled to one of the drive springs and disposed near one of the endcaps, the at least one control button being configured to allow a user to start and stop rotation of the first member.

15. The device of claim 1, wherein the device further comprise a stand that is removably coupled to a bottom portion of the housing.

16. The device of claim 1, wherein the housing comprises first and second endcaps disposed near opposite ends of the central chamber and the device further comprises a first pair of legs that are removably coupled to the first endcap and a second pair of legs that are removably coupled to the second endcap, wherein the first and second pair of legs have legs that are pivotable between an open position to allow the device to stand and a closed position to allow the device to be carried and to form a protective frame for the device.

17. The device of claim 1, wherein the first and second members comprises first and second rollers disposed within the central chamber, having outer surfaces in close proximity to one another and configured to apply the force to the bag when the bag passes therebetween during use.

18. The device of claim 17, wherein the housing further comprises a first set of angled walls on a first side of the rollers defining an entry pathway for the bag between the rollers and a second set of angled walls on an opposite side of the rollers defining an exit pathway out of the rollers for the bag, the first and second set of angled walls also being configured to prevent the bag from coiling around the rollers.

19. The device of claim 17, wherein the rotation assembly further comprises a latch mechanism having a knob having a first engagement surface and a rotatable drive member having a first engagement surface, the drive member being operatively coupled to the spring mechanism and the first roller, the knob being movable between a first position in which the first and second engagement surfaces engage one another and the spring mechanism, the drive member and the at least one roller are operatively coupled and a second position in which the first and second engagement surfaces do not engage one another and the spring mechanism is configured to be recharged.

20. The device of claim 19, wherein the spring mechanism comprises a spool that is rotatably coupled to the housing and a drive spring having a first end coupled to the drive member and a second end coupled to the spool, wherein during the start mode the drive spring is configured to coil around the spool thereby imparting a rotational drive force to the drive member which is translated to the first roller.

21. The device of claim 20, wherein the device further comprises a gearing mechanism having first and second gears that are operatively coupled to the first and second rollers respectively, and the first and second gears are operatively coupled to one another so that the drive force is transferred from the first roller to the second roller during the start mode.

22. The device of claim 1, wherein the control assembly is movable between a locked position and an unlocked position due to actuation of the user interface, wherein, during use, the first member is allowed to rotate when the control assembly is in the unlocked position during the start mode and during recharging of the spring mechanism and the first member is prevented from rotating when the control assembly is in the locked position during the stop mode.

23. The device of claim 1, wherein the user interface of the control mechanism comprises a toggle switch, a slide-switch, a lever or at least one button.

24. The device of claim 1, wherein the spring mechanism comprises at least one spring that is a constant force spring, a clock spring, a self-coiling spring, a variable force spring, a conforce spring, a contorque spring, a torsion spring or a power spring.

25. The device of claim 1, wherein the device further comprises a rotatable crank that is operatively coupled to the first member and the spring mechanism to allow a user to rotate the first member in an opposite direction of a drive direction to remove the bag and to charge the spring mechanism.

26. The device of claim 1, wherein the control mechanism further comprises a latch mechanism that is movable between first and second positions during use due to actuation by a user and the control assembly is movable between first and second positions during use due to actuation of the user interface, wherein during use, the first member is allowed to rotate when the control assembly and the latch mechanism are in the first position and the first member is prevented from rotating when at least one of the control assembly and the latch mechanism is in the second position.

27. A mobile infusion device that does not use gravity to expel fluid from a bag, wherein the mobile infusion device comprises:
a housing including a first portion shaped to define a central chamber in the housing and a second portion shaped to define a first opening in the housing that is in communication with the central chamber and adapted to receive a portion of the bag during use;
a rotation assembly coupled to the housing, the rotation assembly including at least one roller located within the central chamber, a drive member operatively coupled to the at least one roller, and a drive spring operatively coupled to the drive member, the drive spring and the drive member being configured to rotate the at least one roller in order to move the bag and apply a force to a portion of the bag to expel fluid from the bag during use; and
a control mechanism operatively coupled to the rotation assembly, the control mechanism having a control assembly that can be actuated between an unlocked position and a locked position and a user interface for allowing a user to control the actuation of the control assembly, the control assembly allowing the drive member and the at least one roller to rotate or the drive spring to be recharged when the control assembly is in the unlocked position and the control assembly preventing rotation of the drive member and the at least one roller or recharging of the drive spring when the control assembly is in the locked position,
wherein the opening, the central chamber and the at least one roller have a length that is long enough to accommodate bags of various sizes.

28. The device of claim 19, wherein the spring mechanism comprises a drive spring that is located along with the drive member inside the housing.

29. The device of claim 1, wherein the device further comprises an element disposed at a location of the rotation assembly to prevent rotation in the opposite direction of a drive direction after the rotation assembly has been recharged so that tension in the spring mechanism will not be released.

30. The device of claim 1, wherein the device further comprises a standby mode during which the spring mechanism is recharged for future use.

31. The device of claim 1, wherein the housing has a compact, tube-like shape.

32. The device of claim 1, wherein a middle portion of the housing has a smaller diameter than end portions of the housing.

33. The device of claim 1, wherein the housing comprises a groove disposed near each end portion thereof to allow the device to be hung or carried in use.

34. The device of claim 5, wherein the handle comprises an aperture that allows the device to be coupled to another object.

35. A mobile infusion device that can expel fluid from a bag during use, wherein the mobile infusion device comprises:
- a housing including a first portion shaped to define a central chamber in the housing, and a second portion shaped to define a first opening in the housing that is in communication with the central chamber and adapted to receive a portion of the bag during use;
- a rotation assembly coupled to the housing, the rotation assembly including at least one member located within the central chamber and a spring mechanism operatively coupled to the at least one member to rotate the at least one member in order to move the bag and apply a force to a portion of the bag to expel fluid from the bag during use;
- a control mechanism operatively coupled to the rotation assembly, the control mechanism having a control assembly to control rotation of the rotation assembly and a user interface coupled to the control assembly to allow a user to select one of a start mode and a stop mode for the mobile infusion device during use, and
- a first pair of legs that are removably coupled to a first end of the housing and a second pair of legs that are removably coupled to a second end of the housing, the first and second pair of legs having legs that are pivotable between an open position to allow the device to stand and a closed position to allow the device to be carried and to form a protective frame for the device, wherein the opening, the central chamber and the at least one member have a length that is long enough to accommodate bags of various sizes.

36. A mobile infusion device that can expel fluid from a bag during use, wherein the mobile infusion device comprises:
- a housing including:
  - a first portion shaped to define a central chamber in the housing; a second portion shaped to define a first opening in the housing that is in communication with the central chamber and adapted to receive a portion of the bag during use, and
  - a handle disposed along a top portion of the housing;
- a rotation assembly coupled to the housing, the rotation assembly including at least one member located within the central chamber and a spring mechanism operatively coupled to the at least one member to rotate the at least one member in order to move the bag and apply a force to a portion of the bag to expel fluid from the bag during use; and
- a control mechanism operatively coupled to the rotation assembly, the control mechanism having:
  - a control assembly to control rotation of the rotation assembly; and
  - a user interface located near the handle and coupled to the control assembly, the user interface being adapted to allow a user to hold and control the device using one hand and to allow the user to select one of a start mode, a stop mode and a standby mode for the mobile infusion device during use, wherein the opening, the central chamber and the at least one roller have a length that is long enough to accommodate bags of various sizes and in the standby mode the spring mechanism is rechargeable for future use.

* * * * *

UNITED STATES PATENT AND TRADEMARK OFFICE
CERTIFICATE OF CORRECTION

PATENT NO. : 8,715,236 B2
APPLICATION NO. : 13/690862
DATED : May 6, 2014
INVENTOR(S) : Aharon R. Barrelli et al.

It is certified that error appears in the above-identified patent and that said Letters Patent is hereby corrected as shown below:

In the Claims

1. Column 34, line 3, "The device of claim 1, wherein a fourth portion housing" should read
-- The device of claim 1, wherein a fourth portion of the housing --.

2. Column 34, line 39, "having slot with a width that is slightly larger than the thick-" should read
-- having a slot with a width that is slightly larger than the thick- --.

Signed and Sealed this
Twenty-first Day of October, 2014

Michelle K. Lee
*Deputy Director of the United States Patent and Trademark Office*